United States Patent [19]
Ecker et al.

[11] Patent Number: 5,367,065
[45] Date of Patent: Nov. 22, 1994

[54] CONSTITUTIVE TRIPLE RESPONSE GENE AND MUTATIONS

[75] Inventors: Joseph R. Ecker, Erial, N.J.; Joseph J. Kieber, Philadelphia, Pa.

[73] Assignee: The Trustees of the University of Pennsylvania, Philadelphia, Pa.

[21] Appl. No.: 928,464

[22] Filed: Aug. 10, 1992

[51] Int. Cl.$^5$ .................... C07H 17/00; C07H 21/04; C12N 15/00
[52] U.S. Cl. ................. 536/23.6; 536/23.2; 435/172.1
[58] Field of Search ............ 536/23.6, 23.2; 800/200, 205; 71/79; 48/48.27; 435/172.1

[56] References Cited
PUBLICATIONS

Bleecker et al. 1988. Science 241: 1086–1089.
Scott. 1990. Physiol. Plant. 78: 147–152.
Feldman et al. 1987. Mol. Gen. Genet. 208: 1–9.
Guzman et al. 1990. Plant Cell 2: 513–523.
Hanks et al. 1988. Science 241: 42–52.
Koncz et al. 1989. PNAS USA 86: 8467–8471.

*Primary Examiner*—David T. Fox
*Assistant Examiner*—Elizabeth C. Kemmerer
*Attorney, Agent, or Firm*—Woodcock Washburn Kurtz Mackiewicz & Norris

[57] ABSTRACT

The present invention is directed to nucleic acid sequences for constitutive triple response mutants and corresponding amino acid sequences. Several ctr mutations are included within the scope of the present invention. The nucleic acid sequences set forth in SEQUENCE ID NUMBERS 1, and 3–6 as well as amino acid sequences set forth in SEQUENCE ID NUMBERS 1 and 2 are particular embodiments of the present invention.

6 Claims, 7 Drawing Sheets

FIG. 6A

| DOMAIN | I | | | III |
|---|---|---|---|---|
| ctr1 | ------IG | -GSFGTV--- | -WHG---VAV | -K-L----- | F--E---L-- |
| b-raf | ..ITVGQRIG | SGSFGTVYKG | KWHG..DVAV | KMLNVTAPTP | Q.....QLQA | FKNEVGVL.. |
| c-raf | ..VMLSTRIG | SGSFGTVYKG | KWHG..DVAV | KILKVVDPTP | E.....QFQA | FRNEVAVL.. |
| a-raf | ..VQLLKRIG | TGSFGTVFRG | RWHG..DVAV | KVLKVSQPTA | E.....QAQA | FKNEMQVL.. |
| draf-1 | ..ILIGPRIG | SGSFGTVYRA | HWHG..PVAV | KTLNVKTPSP | A...QLQA | FKNEVAML.. |
| dpyk1 | NELEFGQTIG | KGFFGEVKRG | YWRET.DVAI | KIIY....RD | QFKTKSSLVM | FQNEVGIL.. |
| dpyk2 | NDIQFIQKVG | EGAFSEVWEG | WWKGI.HVAI | KKLKIIGDEE | QFKER..... | FI REVQNL.. |
| zmpk1 | ..RKFKVELG | RGESGTVYKG | VLEDDRHVAV | KKLENVRQCK | E.........V | FQAELSVI.. |

| DOMAIN | IV | | V | 100 | 101 |
|---|---|---|---|---|---|
| ctr1 | --RH-NI-- | FMG----T-- | ----IVT- | W----SLY-- | LH------- | -------ID |
| b-raf | RKTRHVNILL | FMGY..STKP | Q...LAIVTQ | WCEGSSLYHH | LHIIETKFEM | IKL.....ID |
| c-raf | RKTRHVNILL | FMGY..MTKD | N...LAIVTQ | WCEGSSLYKH | LHVQETKFQM | FQL.....ID |
| a-raf | RKTRHVNILL | FMGF..MTRP | G...FAIITQ | WCEGSSLYHH | LHVADTRFDM | VQL.....ID |
| draf-1 | KKTRHCNILL | FMGC..VSKP | S...LAIVTQ | WCEGSSLYKH | VHVSETKFKL | NTL.....ID |
| dpyk1 | SKLRHPNVVQ | FLGA..CTAG | GEDHHCIVTE | WMGGGSLRQE | LTD..HFNL | LEQNPHIRLK |
| dpyk2 | KKGNHQNIVM | FIGA..CYKP | A..CIITE | YMAGGSLYNI | LHNPNSSTPK | VKYSFPLVLK |
| zmpk1 | GRINHMNLVR | IWGF..CSEG | SHRLL..VSE | YVENGSLANI | LFSEGGN... | ILLDWEGRFN |

| DOMAIN | VIa | | VIb | | |
|---|---|---|---|---|---|
| ctr1 | --R--A-GM- | YLH------- | D--S--N-FL- | ------- | -------K |
| b-raf | IARQTAGGMD | YLHAK..... | DLKSNNIFLH | E......... | .....DLTVK |
| c-raf | IARQTAQGMD | YLHAK..... | DMKSNNIFLH | E......... | .....GLTVK |
| a-raf | VARQTAQGMD | YLHAK..... | DLKSNNIFLH | E......... | .....GLTVK |
| draf-1 | IGRQVAQGMD | YLHAK..... | DLKSNNIFLH | E......... | .....DLSVK |
| dpyk1 | LALDIAKGMN | YLHGW..... | DLSSRNNILL | DHNIDPKNPL | VSSRQDIKCK |
| dpyk2 | MATDMALGLL | HLHSI..... | DLTSQNILLD | ELG....... | ....NIK |
| zmpk1 | IALGVAKGLA | YLHHE..... | DVKPENILLD | Q......... | ....AFEPK |

FIG. 6B

| DOMAIN | VII | | | VIII | | IX |
|---|---|---|---|---|---|---|
| | | 200 | 201 | | | |
| ctrl | I-DFGL----K | -------- | QL---- | WMAPEV-R-- | --D------ | S-DVY-FGIV |
| b-raf | IGDFGLATVK | SRWSGSHQFE | QL...SGSIL | WMAPEVIR.. | MQDKNPYSFQ | S..DVYAFGIV |
| c-raf | IGDFGLATVK | SRWSGSQQVE | QP...TGSVL | WMAPEVIR.. | MQDNNPFSFQ | S..DVYSYGIV |
| a-raf | IGDFGLATVK | TRWSGAQPLE | QP...SGSVL | WMAAEVIR.. | MQDPNPYSFQ | S..DVYAYGYV |
| draf-1 | IGDFGLATAK | TRWSGEKQAN | QP...TGSIL | WMAPEVIR.. | MQELNPYSFQ | S..DVYAFGIV |
| dpyk1 | ISDFGLSRLK | KEQASQMTQS | VG....IP | YMAPEVFK.. | ..G.DSNSEK | S..DVYSYGMV |
| dpyk2 | ISDFGLSAEK | SREGSMTMTN | GG..ICNPR | WRPPELTK.. | .NLGHYSEK | V..DVYCFSLV |
| zmpk1 | ITDFGLVKLL | NRGGSTQNVS | HV...RGTLG | YIAPEWVS.. | SL..PITAK | V..DVYSYGVV |

| DOMAIN | | | X | | | |
|---|---|---|---|---|---|---|
| ctrl | L-E-L----P | -------- | Q----VG-- | -------- | ----L---- | --C------- |
| b-raf | LYELMTGQLP | YSNI..NNRD | QIIFMVGRGY | LSPDLSKVRS | NCPKAMKRLM | AECLKKKRDE |
| c-raf | LYELMTGELP | YSHI..NNRD | QIIFMVGRGY | ASPDLSKLYK | NCPKAMKRLV | ADCVKKVKEE |
| a-raf | LYELMTGSLP | YSHI..GCRD | QIIFMVGRGY | LSPDLSKISS | NCPKAMRRLL | SDCLKFQREE |
| draf-1 | MYELLAECLP | YGHI..SNKD | QILFMVGRGL | LRPDMSQVRS | DARRHSKRLA | EDCIKYTPKD |
| dpyk1 | LFELLTSDEP | QQDM..KPMK | MAHLAATESY | RPP....IPL | TTSSKWKEIL | TQCWDSNPDS |
| dpyk2 | VWEILTGEIP | FSDL..DGSQ | RSAQVAYAGL | RPP....IPE | YCDPELKLLL | TQCWEADPND |
| zmpk1 | LLELLTGTRV | SELV..GGTD | EV.....HSM | LRKLVRMLSA | KLEGEEQSWI | DGYLDSKLNR |

| DOMAIN | XI |
|---|---|
| | 301 |
| ctrl | RP-F----- |
| b-raf | RPLFPQILAS |
| c-raf | RPLFPQILSS |
| a-raf | RPLFPQILAT |
| draf-1 | RPLFRPLLNM |
| dpyk1 | RPTFKQIIVH LKEMEDQGV. |
| dpyk2 | RPPFTYIVNK LKEISWNNP. |
| zmpk1 | RPVNYQARTL .......... |

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2890 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 118..2583

( x i ) SEQUENCE DESCRIPTION: SEQ ID NO:1:

```
AGAGAAACAA  GTGGCTAGCT  AGCTCGCCAA  ACTTCTTCAA  CAATGGCGGT  TTCCTAGGGT         60

TTGATGTTTA  TATGATCGGG  AAACTCTCTC  ATCTAGATCG  CGATAACTCT  CTTTTCC          117

ATG  GAA  ATG  CCC  GGT  AGA  AGA  TCT  AAT  TAC  ACT  TTG  CTT  AGT  CAA  TTT      165
Met  Glu  Met  Pro  Gly  Arg  Arg  Ser  Asn  Tyr  Thr  Leu  Leu  Ser  Gln  Phe
 1              5                       10                      15
```

-continued

| | | | | | | | | | | | | | | | | |
|---|---|---|---|---|---|---|---|---|---|---|---|---|---|---|---|---|
| TCT | GAC | GAT | CAG | GTG | TCA | GTT | TCC | GTC | ACC | GGA | GCT | CCT | CCG | CCT | CAC | 213 |
| Ser | Asp | Asp | Gln 20 | Val | Ser | Val | Ser 25 | Val | Thr | Gly | Ala | Pro | Pro 30 | Pro | His | |
| TAT | GAT | TCC | TTG | TCG | AGC | GAA | AAC | AGG | AGC | AAC | CAT | AAC | AGC | GGG | AAC | 261 |
| Tyr | Asp | Ser 35 | Leu | Ser | Ser | Glu | Asn 40 | Arg | Ser | Asn | His | Asn 45 | Ser | Gly | Asn | |
| ACC | GGG | AAA | GCT | AAG | GCG | GAG | AGA | GGC | GGA | TTT | GAT | TGG | GAT | CCT | AGC | 309 |
| Thr | Gly 50 | Lys | Ala | Lys | Ala | Glu 55 | Arg | Gly | Gly | Phe | Asp 60 | Trp | Asp | Pro | Ser | |
| GGT | GGT | GGT | GGT | GGT | GAT | CAT | AGG | TTG | AAT | AAT | CAA | CCG | AAT | CGG | GTT | 357 |
| Gly 65 | Gly | Gly | Gly | Gly | Asp 70 | His | Arg | Leu | Asn | Asn 75 | Gln | Pro | Asn | Arg | Val 80 | |
| GGG | AAT | AAT | ATG | TAT | GCT | TCG | TCT | CTA | GGG | TTG | CAA | AGG | CAA | TCC | AGT | 405 |
| Gly | Asn | Asn | Met | Tyr 85 | Ala | Ser | Ser | Leu | Gly 90 | Leu | Gln | Arg | Gln | Ser 95 | Ser | |
| GGG | AGT | AGT | TTC | GGT | GAG | AGC | TCT | TTG | TCT | GGG | GAT | TAT | TAC | ATG | CCT | 453 |
| Gly | Ser | Ser | Phe 100 | Gly | Glu | Ser | Ser | Leu 105 | Ser | Gly | Asp | Tyr | Tyr 110 | Met | Pro | |
| ACG | CTT | TCT | GCG | GCG | GCT | AAC | GAG | ATC | GAA | TCT | GTT | GGA | TTT | CCT | CAA | 501 |
| Thr | Leu | Ser 115 | Ala | Ala | Ala | Asn | Glu 120 | Ile | Glu | Ser | Val | Gly 125 | Phe | Pro | Gln | |
| GAT | GAT | GGG | TTT | AGG | CTT | GGA | TTT | GGT | GGT | GGT | GGA | GGA | GAT | TTG | AGG | 549 |
| Asp | Asp 130 | Gly | Phe | Arg | Leu | Gly 135 | Phe | Gly | Gly | Gly | Gly 140 | Gly | Asp | Leu | Arg | |
| ATA | CAG | ATG | GCG | GCG | GAC | TCC | GCT | GGA | GGG | TCT | TCA | TCT | GGG | AAG | AGC | 597 |
| Ile 145 | Gln | Met | Ala | Ala | Asp 150 | Ser | Ala | Gly | Gly | Ser 155 | Ser | Ser | Gly | Lys | Ser 160 | |
| TGG | GCG | CAG | CAG | ACG | GAG | GAG | AGT | TAT | CAG | CTG | CAG | CTT | GCA | TTG | GCG | 645 |
| Trp | Ala | Gln | Gln | Thr 165 | Glu | Glu | Ser | Tyr | Gln 170 | Leu | Gln | Leu | Ala | Leu 175 | Ala | |
| TTA | AGG | CTT | TCG | TCG | GAG | GCT | ACT | TGT | GCC | GAC | GAT | CCG | AAC | TTT | CTG | 693 |
| Leu | Arg | Leu | Ser 180 | Ser | Glu | Ala | Thr | Cys 185 | Ala | Asp | Asp | Pro | Asn 190 | Phe | Leu | |
| GAT | CCT | GTA | CCG | GAC | GAG | TCT | GCT | TTA | CGG | ACT | TCG | CCA | AGT | TCA | GCC | 741 |
| Asp | Pro | Val 195 | Pro | Asp | Glu | Ser | Ala 200 | Leu | Arg | Thr | Ser | Pro 205 | Ser | Ser | Ala | |
| GAA | ACC | GTT | TCA | CAT | CGT | TTC | TGG | GTT | AAT | GGC | TGC | TTA | TCG | TAC | TAT | 789 |
| Glu | Thr 210 | Val | Ser | His | Arg | Phe 215 | Trp | Val | Asn | Gly | Cys 220 | Leu | Ser | Tyr | Tyr | |
| GAT | AAA | GTT | CCT | GAT | GGG | TTT | TAT | ATG | ATG | AAT | GGT | CTG | GAT | CCC | TAT | 837 |
| Asp 225 | Lys | Val | Pro | Asp | Gly 230 | Phe | Tyr | Met | Met | Asn 235 | Gly | Leu | Asp | Pro | Tyr 240 | |
| ATT | TGG | ACC | TTA | TGC | ATC | GAC | CTG | CAT | GAA | AGT | GGT | CGC | ATC | CCT | TCA | 885 |
| Ile | Trp | Thr | Leu | Cys 245 | Ile | Asp | Leu | His | Glu 250 | Ser | Gly | Arg | Ile | Pro 255 | Ser | |
| ATT | GAA | TCA | TTA | AGA | GCT | GTT | GAT | TCT | GGT | GTT | GAT | TCT | TCG | CTT | GAA | 933 |
| Ile | Glu | Ser | Leu 260 | Arg | Ala | Val | Asp | Ser 265 | Gly | Val | Asp | Ser | Ser 270 | Leu | Glu | |
| GCG | ATC | ATA | GTT | GAT | AGG | CGT | AGT | GAT | CCA | GCC | TTC | AAG | GAA | CTT | CAC | 981 |
| Ala | Ile | Ile 275 | Val | Asp | Arg | Arg | Ser 280 | Asp | Pro | Ala | Phe | Lys 285 | Glu | Leu | His | |
| AAT | AGA | GTC | CAC | GAC | ATA | TCT | TGT | AGC | TGC | ATT | ACC | ACA | AAA | GAG | GTT | 1029 |
| Asn | Arg 290 | Val | His | Asp | Ile | Ser 295 | Cys | Ser | Cys | Ile | Thr 300 | Thr | Lys | Glu | Val | |
| GTT | GAT | CAG | CTG | GCA | AAG | CTT | ATC | TGC | AAT | CGT | ATG | GGG | GGT | CCA | GTT | 1077 |
| Val | Asp | Gln | Leu | Ala 310 | Lys | Leu | Ile | Cys | Asn 315 | Arg | Met | Gly | Gly | Pro 320 | Val | |
| ATC | ATG | GGG | GAA | GAT | GAG | TTG | GTT | CCC | ATG | TGG | AAG | GAG | TGC | ATT | GAT | 1125 |
| Ile | Met | Gly | Glu | Asp 325 | Glu | Leu | Val | Pro | Met 330 | Trp | Lys | Glu | Cys | Ile 335 | Asp | |
| GGT | CTA | AAA | GAA | ATC | TTT | AAA | GTG | GTG | GTT | CCC | ATA | GGT | AGC | CTC | TCT | 1173 |

Val 305

-continued

| | | | | | | | | | | | | | | | | |
|---|---|---|---|---|---|---|---|---|---|---|---|---|---|---|---|---|
| | Gly | Leu | Lys | Glu | Ile | Phe | Lys | Val | Val | Pro | Ile | Gly | Ser | Leu | Ser | |
| | | | 340 | | | | | 345 | | | | | 350 | | | |
| GTT | GGA | CTC | TGC | AGA | CAT | CGA | GCT | TTA | CTC | TTC | AAA | GTA | CTG | GCT | GAC | 1221 |
| Val | Gly | Leu | Cys | Arg | His | Arg | Ala | Leu | Leu | Phe | Lys | Val | Leu | Ala | Asp | |
| | | 355 | | | | 360 | | | | | 365 | | | | | |
| ATA | ATT | GAT | TTA | CCC | TGT | CGA | ATT | GCC | AAA | GGA | TGT | AAA | TAT | TGT | AAT | 1269 |
| Ile | Ile | Asp | Leu | Pro | Cys | Arg | Ile | Ala | Lys | Gly | Cys | Lys | Tyr | Cys | Asn | |
| | 370 | | | | | 375 | | | | | 380 | | | | | |
| AGA | GAC | GAT | GCC | GCT | TCG | TGC | CTT | GTC | AGG | TTT | GGG | CTT | GAT | AGG | GAG | 1317 |
| Arg | Asp | Asp | Ala | Ala | Ser | Cys | Leu | Val | Arg | Phe | Gly | Leu | Asp | Arg | Glu | |
| 385 | | | | | 390 | | | | | 395 | | | | | 400 | |
| TAC | CTG | GTT | GAT | TTA | GTA | GGA | AAG | CCA | GGT | CAC | TTA | TGG | GAG | CCT | GAT | 1365 |
| Tyr | Leu | Val | Asp | Leu | Val | Gly | Lys | Pro | Gly | His | Leu | Trp | Glu | Pro | Asp | |
| | | | | 405 | | | | | 410 | | | | | 415 | | |
| TCC | TTG | CTA | AAT | GGT | CCT | TCA | TCT | ATC | TCA | ATT | TCT | TCT | CCT | CTG | CGG | 1413 |
| Ser | Leu | Leu | Asn | Gly | Pro | Ser | Ser | Ile | Ser | Ile | Ser | Ser | Pro | Leu | Arg | |
| | | | 420 | | | | | 425 | | | | | 430 | | | |
| TTT | CCA | CGA | CCA | AAG | CCA | GTT | GAA | CCC | GCA | GTC | GAT | TTT | AGG | TTA | CTA | 1461 |
| Phe | Pro | Arg | Pro | Lys | Pro | Val | Glu | Pro | Ala | Val | Asp | Phe | Arg | Leu | Leu | |
| | | 435 | | | | | 440 | | | | | 445 | | | | |
| GCC | AAA | CAA | TAT | TTC | TCC | GAT | AGC | CAG | TCT | CTT | AAT | CTT | GTT | TTC | GAT | 1509 |
| Ala | Lys | Gln | Tyr | Phe | Ser | Asp | Ser | Gln | Ser | Leu | Asn | Leu | Val | Phe | Asp | |
| | 450 | | | | | 455 | | | | | 460 | | | | | |
| CCT | GCA | TCA | GAT | GAT | ATG | GGA | TTC | TCA | ATG | TTT | CAT | AGG | CAA | TAT | GAT | 1557 |
| Pro | Ala | Ser | Asp | Asp | Met | Gly | Phe | Ser | Met | Phe | His | Arg | Gln | Tyr | Asp | |
| 465 | | | | | 470 | | | | | 475 | | | | | 480 | |
| AAT | CCG | GGT | GGA | GAG | AAT | GAC | GCA | TTG | GCA | GAA | AAT | GGT | GGT | GGG | TCT | 1605 |
| Asn | Pro | Gly | Gly | Glu | Asn | Asp | Ala | Leu | Ala | Glu | Asn | Gly | Gly | Gly | Ser | |
| | | | | 485 | | | | | 490 | | | | | 495 | | |
| TTG | CCA | CCC | AGT | GCT | AAT | ATG | CCT | CCA | CAG | AAC | ATG | ATG | CGT | GCG | TCA | 1653 |
| Leu | Pro | Pro | Ser | Ala | Asn | Met | Pro | Pro | Gln | Asn | Met | Met | Arg | Ala | Ser | |
| | | | 500 | | | | | 505 | | | | | 510 | | | |
| AAT | CAA | ATT | GAA | GCA | GCA | CCT | ATG | AAT | GCC | CCA | CCA | ATC | AGT | CAG | CCA | 1701 |
| Asn | Gln | Ile | Glu | Ala | Ala | Pro | Met | Asn | Ala | Pro | Pro | Ile | Ser | Gln | Pro | |
| | | 515 | | | | | 520 | | | | | 525 | | | | |
| GTT | CCA | AAC | AGG | GCA | AAT | AGG | GAA | CTT | GGA | CTT | GAT | GGT | GAT | GAT | ATG | 1749 |
| Val | Pro | Asn | Arg | Ala | Asn | Arg | Glu | Leu | Gly | Leu | Asp | Gly | Asp | Asp | Met | |
| | 530 | | | | | 535 | | | | | 540 | | | | | |
| GAC | ATC | CCG | TGG | TGT | GAT | CTT | AAT | ATA | AAA | GAA | AAG | ATT | GGA | GCA | GGT | 1797 |
| Asp | Ile | Pro | Trp | Cys | Asp | Leu | Asn | Ile | Lys | Glu | Lys | Ile | Gly | Ala | Gly | |
| 545 | | | | | 550 | | | | | 555 | | | | | 560 | |
| TCC | TTT | GGC | ACT | GTC | CAC | CGT | GCT | GAG | TGG | CAT | GGC | TCG | GAT | GTT | GCT | 1845 |
| Ser | Phe | Gly | Thr | Val | His | Arg | Ala | Glu | Trp | His | Gly | Ser | Asp | Val | Ala | |
| | | | | 565 | | | | | 570 | | | | | 575 | | |
| GTG | AAA | ATT | CTC | ATG | GAG | CAA | GAC | TTC | CAT | GCT | GAG | CGT | GTT | AAT | GAG | 1893 |
| Val | Lys | Ile | Leu | Met | Glu | Gln | Asp | Phe | His | Ala | Glu | Arg | Val | Asn | Glu | |
| | | | 580 | | | | | 585 | | | | | 590 | | | |
| TTC | TTA | AGA | GAG | GTT | GCG | ATA | ATG | AAA | CGC | CTT | CGC | CAC | CCT | AAC | ATT | 1941 |
| Phe | Leu | Arg | Glu | Val | Ala | Ile | Met | Lys | Arg | Leu | Arg | His | Pro | Asn | Ile | |
| | | 595 | | | | | 600 | | | | | 605 | | | | |
| GTT | CTC | TTC | ATG | GGT | GCG | GTC | ACT | CAA | CCT | CCA | AAT | TTG | TCA | ATA | GTG | 1989 |
| Val | Leu | Phe | Met | Gly | Ala | Val | Thr | Gln | Pro | Pro | Asn | Leu | Ser | Ile | Val | |
| | 610 | | | | | 615 | | | | | 620 | | | | | |
| ACA | GAA | TAT | TTG | TCA | AGA | GGT | AGT | TTA | TAC | AGA | CTT | TTG | CAT | AAA | AGT | 2037 |
| Thr | Glu | Tyr | Leu | Ser | Arg | Gly | Ser | Leu | Tyr | Arg | Leu | Leu | His | Lys | Ser | |
| 625 | | | | | 630 | | | | | 635 | | | | | 640 | |
| GGA | GCA | AGG | GAG | CAA | TTA | GAT | GAG | AGA | CGT | CGC | CTG | AGT | ATG | GCT | TAT | 2085 |
| Gly | Ala | Arg | Glu | Gln | Leu | Asp | Glu | Arg | Arg | Arg | Leu | Ser | Met | Ala | Tyr | |
| | | | | 645 | | | | | 650 | | | | | 655 | | |
| GAT | GTG | GCT | AAG | GGA | ATG | AAT | TAT | CTT | CAC | AAT | CGC | AAT | CCT | CCA | ATT | 2133 |
| Asp | Val | Ala | Lys | Gly | Met | Asn | Tyr | Leu | His | Asn | Arg | Asn | Pro | Pro | Ile | |
| | | | | 660 | | | | | 665 | | | | | 670 | | |

| | | | | | | | | | | | | | | | | |
|---|---|---|---|---|---|---|---|---|---|---|---|---|---|---|---|---|
| GTG | CAT | AGA | GAT | CTA | AAA | TCT | CCA | AAC | TTA | TTG | GTT | GAC | AAA | AAA | TAT | 2181 |
| Val | His | Arg | Asp | Leu | Lys | Ser | Pro | Asn | Leu | Leu | Val | Asp | Lys | Lys | Tyr | |
| | | 675 | | | | | 680 | | | | | 685 | | | | |
| ACA | GTC | AAG | GTT | TGT | GAT | TTT | GGT | CTC | TCG | CGA | TTG | AAG | GCC | AGC | ACG | 2229 |
| Thr | Val | Lys | Val | Cys | Asp | Phe | Gly | Leu | Ser | Arg | Leu | Lys | Ala | Ser | Thr | |
| | 690 | | | | | 695 | | | | | 700 | | | | | |
| TTT | CTT | TCC | TCG | AAG | TCA | GCA | GCT | GGA | ACC | CCC | GAG | TGG | ATG | GCA | CCA | 2277 |
| Phe | Leu | Ser | Ser | Lys | Ser | Ala | Ala | Gly | Thr | Pro | Glu | Trp | Met | Ala | Pro | |
| 705 | | | | | 710 | | | | | 715 | | | | | 720 | |
| GAA | GTC | CTG | CGA | GAT | GAG | CCG | TCT | AAT | GAA | AAG | TCA | GAT | GTG | TAC | AGC | 2325 |
| Glu | Val | Leu | Arg | Asp | Glu | Pro | Ser | Asn | Glu | Lys | Ser | Asp | Val | Tyr | Ser | |
| | | | | 725 | | | | | 730 | | | | | 735 | | |
| TTC | GGG | GTC | ATC | TTG | TGG | GAG | CTT | GCT | ACA | TTG | CAA | CAA | CCA | TGG | GGT | 2373 |
| Phe | Gly | Val | Ile | Leu | Trp | Glu | Leu | Ala | Thr | Leu | Gln | Gln | Pro | Trp | Gly | |
| | | | 740 | | | | | 745 | | | | | 750 | | | |
| AAC | TTA | AAT | CCG | GCT | CAG | GTT | GTA | GCT | GCG | GTT | GGT | TTC | AAG | TGT | AAA | 2421 |
| Asn | Leu | Asn | Pro | Ala | Gln | Val | Val | Ala | Ala | Val | Gly | Phe | Lys | Cys | Lys | |
| | | 755 | | | | | 760 | | | | | 765 | | | | |
| CGG | CTG | GAG | ATC | CCG | CGT | AAT | CTG | AAT | CCT | CAG | GTT | GCA | GCC | ATA | ATC | 2469 |
| Arg | Leu | Glu | Ile | Pro | Arg | Asn | Leu | Asn | Pro | Gln | Val | Ala | Ala | Ile | Ile | |
| | | 770 | | | | | 775 | | | | | 780 | | | | |
| GAG | GGT | TGT | TGG | ACC | AAT | GAG | CCA | TGG | AAG | CGT | CCA | TCA | TTT | GCA | ACT | 2517 |
| Glu | Gly | Cys | Trp | Thr | Asn | Glu | Pro | Trp | Lys | Arg | Pro | Ser | Phe | Ala | Thr | |
| 785 | | | | | 790 | | | | | 795 | | | | | 800 | |
| ATA | ATG | GAC | TTG | CTA | AGA | CCA | TTG | ATC | AAA | TCA | GCG | GTT | CCT | CCG | CCC | 2565 |
| Ile | Met | Asp | Leu | Leu | Arg | Pro | Leu | Ile | Lys | Ser | Ala | Val | Pro | Pro | Pro | |
| | | | | 805 | | | | | 810 | | | | | 815 | | |
| AAC | CGC | TCG | GAT | TTG | TAAAATACCC | CCGGTCCATT | CAAAAGTTGT | TATAATCATG | | | | 2620 |
| Asn | Arg | Ser | Asp | Leu | | | | | | | | |
| | | | | 820 | | | | | | | | |

ATATGCACAT ATACTCTCAG CATTCTTTTG CTGCCCAGGA GGGAGACACT AGTTAAGATA 2680

TAGCTTTAAA GGTACATTCC TCATGAGCTA TCAATCATAT CCTACAGAAT CCCATGGTTT 2740

TTATACATGT ATTATTTTTG CGATCTTTGT CTGCTGTTTT GTTCCCTTTT TAATGTTGCA 2800

GATTGTTAAA ATGTACATGA CTATTGTCAC AGGGAGGAAA AAAAAATGTA GTAATGGAAA 2860

CAATGTGAGG GATATAATCT ATCTATCTAG 2890

( 2 ) INFORMATION FOR SEQ ID NO:2:

( i ) SEQUENCE CHARACTERISTICS:
        ( A ) LENGTH: 821 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Glu | Met | Pro | Gly | Arg | Arg | Ser | Asn | Tyr | Thr | Leu | Leu | Ser | Gln | Phe |
| 1 | | | | 5 | | | | | 10 | | | | | 15 | |
| Ser | Asp | Asp | Gln | Val | Ser | Val | Ser | Val | Thr | Gly | Ala | Pro | Pro | Pro | His |
| | | | 20 | | | | | 25 | | | | | 30 | | |
| Tyr | Asp | Ser | Leu | Ser | Ser | Glu | Asn | Arg | Ser | Asn | His | Asn | Ser | Gly | Asn |
| | | | 35 | | | | | 40 | | | | | 45 | | |
| Thr | Gly | Lys | Ala | Lys | Ala | Glu | Arg | Gly | Gly | Phe | Asp | Trp | Asp | Pro | Ser |
| | 50 | | | | | 55 | | | | | 60 | | | | |
| Gly | Gly | Gly | Gly | Gly | Asp | His | Arg | Leu | Asn | Asn | Gln | Pro | Asn | Arg | Val |
| 65 | | | | | 70 | | | | | 75 | | | | | 80 |
| Gly | Asn | Asn | Met | Tyr | Ala | Ser | Ser | Leu | Gly | Leu | Gln | Arg | Gln | Ser | Ser |
| | | | | 85 | | | | | 90 | | | | | 95 | |
| Gly | Ser | Ser | Phe | Gly | Glu | Ser | Ser | Leu | Ser | Gly | Asp | Tyr | Tyr | Met | Pro |

```
                    100                        105                        110
Thr Leu Ser Ala Ala Ala Asn Glu Ile Glu Ser Val Gly Phe Pro Gln
        115                 120                 125
Asp Asp Gly Phe Arg Leu Gly Phe Gly Gly Gly Gly Gly Asp Leu Arg
    130                 135                 140
Ile Gln Met Ala Ala Asp Ser Ala Gly Gly Ser Ser Ser Gly Lys Ser
145                 150                 155                     160
Trp Ala Gln Gln Thr Glu Glu Ser Tyr Gln Leu Gln Leu Ala Leu Ala
                165                 170                 175
Leu Arg Leu Ser Ser Glu Ala Thr Cys Ala Asp Asp Pro Asn Phe Leu
            180                 185                 190
Asp Pro Val Pro Asp Glu Ser Ala Leu Arg Thr Ser Pro Ser Ser Ala
            195                 200                 205
Glu Thr Val Ser His Arg Phe Trp Val Asn Gly Cys Leu Ser Tyr Tyr
        210                 215                 220
Asp Lys Val Pro Asp Gly Phe Tyr Met Met Asn Gly Leu Asp Pro Tyr
225                 230                 235                     240
Ile Trp Thr Leu Cys Ile Asp Leu His Glu Ser Gly Arg Ile Pro Ser
                245                 250                 255
Ile Glu Ser Leu Arg Ala Val Asp Ser Gly Val Asp Ser Ser Leu Glu
            260                 265                 270
Ala Ile Ile Val Asp Arg Arg Ser Asp Pro Ala Phe Lys Glu Leu His
        275                 280                 285
Asn Arg Val His Asp Ile Ser Cys Ser Cys Ile Thr Thr Lys Glu Val
    290                 295                 300
Val Asp Gln Leu Ala Lys Leu Ile Cys Asn Arg Met Gly Gly Pro Val
305                 310                 315                     320
Ile Met Gly Glu Asp Glu Leu Val Pro Met Trp Lys Glu Cys Ile Asp
                325                 330                 335
Gly Leu Lys Glu Ile Phe Lys Val Val Pro Ile Gly Ser Leu Ser
            340                 345                 350
Val Gly Leu Cys Arg His Arg Ala Leu Leu Phe Lys Val Leu Ala Asp
            355                 360                 365
Ile Ile Asp Leu Pro Cys Arg Ile Ala Lys Gly Cys Lys Tyr Cys Asn
    370                 375                 380
Arg Asp Asp Ala Ala Ser Cys Leu Val Arg Phe Gly Leu Asp Arg Glu
385                 390                 395                     400
Tyr Leu Val Asp Leu Val Gly Lys Pro Gly His Leu Trp Glu Pro Asp
                405                 410                 415
Ser Leu Leu Asn Gly Pro Ser Ser Ile Ser Ile Ser Ser Pro Leu Arg
            420                 425                 430
Phe Pro Arg Pro Lys Pro Val Glu Pro Ala Val Asp Phe Arg Leu Leu
        435                 440                 445
Ala Lys Gln Tyr Phe Ser Asp Ser Gln Ser Leu Asn Leu Val Phe Asp
    450                 455                 460
Pro Ala Ser Asp Asp Met Gly Phe Ser Met Phe His Arg Gln Tyr Asp
465                 470                 475                     480
Asn Pro Gly Gly Glu Asn Asp Ala Leu Ala Glu Asn Gly Gly Gly Ser
                485                 490                 495
Leu Pro Pro Ser Ala Asn Met Pro Pro Gln Asn Met Met Arg Ala Ser
            500                 505                 510
Asn Gln Ile Glu Ala Ala Pro Met Asn Ala Pro Pro Ile Ser Gln Pro
        515                 520                 525
Val Pro Asn Arg Ala Asn Arg Glu Leu Gly Leu Asp Gly Asp Asp Met
    530                 535                 540
```

| Asp 545 | Ile | Pro | Trp | Cys | Asp 550 | Leu | Asn | Ile | Lys | Glu 555 | Lys | Ile | Gly | Ala | Gly 560 |
| Ser | Phe | Gly | Thr | Val 565 | His | Arg | Ala | Glu | Trp 570 | His | Gly | Ser | Asp | Val 575 | Ala |
| Val | Lys | Ile | Leu 580 | Met | Glu | Gln | Asp | Phe 585 | His | Ala | Glu | Arg | Val 590 | Asn | Glu |
| Phe | Leu | Arg 595 | Glu | Val | Ala | Ile | Met 600 | Lys | Arg | Leu | Arg | His 605 | Pro | Asn | Ile |
| Val | Leu 610 | Phe | Met | Gly | Ala | Val 615 | Thr | Gln | Pro | Pro | Asn 620 | Leu | Ser | Ile | Val |
| Thr 625 | Glu | Tyr | Leu | Ser | Arg 630 | Gly | Ser | Leu | Tyr | Arg 635 | Leu | Leu | His | Lys | Ser 640 |
| Gly | Ala | Arg | Glu | Gln 645 | Leu | Asp | Glu | Arg | Arg 650 | Arg | Leu | Ser | Met | Ala 655 | Tyr |
| Asp | Val | Ala | Lys 660 | Gly | Met | Asn | Tyr | Leu 665 | His | Asn | Arg | Asn | Pro 670 | Pro | Ile |
| Val | His | Arg 675 | Asp | Leu | Lys | Ser | Pro 680 | Asn | Leu | Leu | Val | Asp 685 | Lys | Lys | Tyr |
| Thr | Val 690 | Lys | Val | Cys | Asp | Phe 695 | Gly | Leu | Ser | Arg | Leu 700 | Lys | Ala | Ser | Thr |
| Phe 705 | Leu | Ser | Ser | Lys | Ser 710 | Ala | Ala | Gly | Thr | Pro 715 | Glu | Trp | Met | Ala | Pro 720 |
| Glu | Val | Leu | Arg | Asp 725 | Glu | Pro | Ser | Asn | Glu 730 | Lys | Ser | Asp | Val | Tyr 735 | Ser |
| Phe | Gly | Val | Ile 740 | Leu | Trp | Glu | Leu | Ala 745 | Thr | Leu | Gln | Gln | Pro 750 | Trp | Gly |
| Asn | Leu | Asn 755 | Pro | Ala | Gln | Val | Val 760 | Ala | Ala | Val | Gly | Phe 765 | Lys | Cys | Lys |
| Arg | Leu 770 | Glu | Ile | Pro | Arg | Asn 775 | Leu | Asn | Pro | Gln | Val 780 | Ala | Ala | Ile | Ile |
| Glu 785 | Gly | Cys | Trp | Thr | Asn 790 | Glu | Pro | Trp | Lys | Arg 795 | Pro | Ser | Phe | Ala | Thr 800 |
| Ile | Met | Asp | Leu | Leu 805 | Arg | Pro | Leu | Ile | Lys 810 | Ser | Ala | Val | Pro | Pro 815 | Pro |
| Asn | Arg | Ser | Asp 820 | Leu | | | | | | | | | | | |

( 2 ) INFORMATION FOR SEQ ID NO:3:

( i ) SEQUENCE CHARACTERISTICS:
        ( A ) LENGTH: 5890 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: intron
        ( B ) LOCATION: 1..353

( i x ) FEATURE:
        ( A ) NAME/KEY: exon
        ( B ) LOCATION: 354..1001

( i x ) FEATURE:
        ( A ) NAME/KEY: intron
        ( B ) LOCATION: 1002..1176

( i x ) FEATURE:
        ( A ) NAME/KEY: exon
        ( B ) LOCATION: 1177..1477

( i x ) FEATURE:
    ( A ) NAME/KEY: intron
    ( B ) LOCATION: 1478..1574

( i x ) FEATURE:
    ( A ) NAME/KEY: exon
    ( B ) LOCATION: 1575..1719

( i x ) FEATURE:
    ( A ) NAME/KEY: intron
    ( B ) LOCATION: 1720..1936

( i x ) FEATURE:
    ( A ) NAME/KEY: exon
    ( B ) LOCATION: 1937..2038

( i x ) FEATURE:
    ( A ) NAME/KEY: intron
    ( B ) LOCATION: 2039..2173

( i x ) FEATURE:
    ( A ) NAME/KEY: exon
    ( B ) LOCATION: 2174..2379

( i x ) FEATURE:
    ( A ) NAME/KEY: intron
    ( B ) LOCATION: 2380..2736

( i x ) FEATURE:
    ( A ) NAME/KEY: exon
    ( B ) LOCATION: 2737..3012

( i x ) FEATURE:
    ( A ) NAME/KEY: intron
    ( B ) LOCATION: 3013..3202

( i x ) FEATURE:
    ( A ) NAME/KEY: exon
    ( B ) LOCATION: 3203..3243

( i x ) FEATURE:
    ( A ) NAME/KEY: intron
    ( B ) LOCATION: 3244..3519

( i x ) FEATURE:
    ( A ) NAME/KEY: exon
    ( B ) LOCATION: 3520..3588

( i x ) FEATURE:
    ( A ) NAME/KEY: intron
    ( B ) LOCATION: 3589..3668

( i x ) FEATURE:
    ( A ) NAME/KEY: exon
    ( B ) LOCATION: 3669..3769

( i x ) FEATURE:
    ( A ) NAME/KEY: intron
    ( B ) LOCATION: 3770..3858

( i x ) FEATURE:
    ( A ) NAME/KEY: exon
    ( B ) LOCATION: 3859..3943

( i x ) FEATURE:
    ( A ) NAME/KEY: intron
    ( B ) LOCATION: 3944..4037

( i x ) FEATURE:
    ( A ) NAME/KEY: exon
    ( B ) LOCATION: 4038..4136

( i x ) FEATURE:
    ( A ) NAME/KEY: intron
    ( B ) LOCATION: 4137..4369

( i x ) FEATURE:
    ( A ) NAME/KEY: exon
    ( B ) LOCATION: 4370..4438

( i x ) FEATURE:
    ( A ) NAME/KEY: intron ( B ) LOCATION: 4439..4541

( i x ) FEATURE:
(A) NAME/KEY: exon
(B) LOCATION: 4542..4673

( i x ) FEATURE:
(A) NAME/KEY: intron
(B) LOCATION: 4674..4787

( i x ) FEATURE:
(A) NAME/KEY: exon
(B) LOCATION: 4788..4882

( i x ) FEATURE:
(A) NAME/KEY: intron
(B) LOCATION: 4883..4959

( i x ) FEATURE:
(A) NAME/KEY: exon
(B) LOCATION: 4960..5056

( i x ) FEATURE:
(A) NAME/KEY: intron
(B) LOCATION: 5057..5890

( x i ) SEQUENCE DESCRIPTION: SEQ ID NO:3:

| | | | | | | |
|---|---|---|---|---|---|---|
| GCACACTAAA | TTGGAGAATT | GTTTTGACCC | AAAATAAAAA | AAATGTCAAA | GTTCCATAAA | 60 |
| GAAGGAGGAC | ACAAGAGGAA | TATAACGAAA | TTATCAACAG | AGACGCACCG | AGTAAGTTTA | 120 |
| TTTCCTATGA | TAACGCCCAA | ACACAAAAAA | AATCCAATTC | CATTAGAGAG | AGAGAGAGAG | 180 |
| AGAGAGAGAG | AGAGAGACTT | TTTTAGAAAG | TACACAAAAA | AAATGAAAAA | CTAGAGAGAG | 240 |
| AAACAAGTGG | CTAGCTAGCT | CGCCAAACTT | CTTCAACAAT | GGCGGTTTCC | TAGGGTTTGA | 300 |
| TGTTTATATG | ATCGGGAAAC | TCTCTCATCT | AGATCGCGAT | AACTCTCTTT | TCCATGGAAA | 360 |
| TGCCCGGTAG | AAGATCTAAT | TACACTTTGC | TTAGTCAATT | TTCTGACGAT | CAGGTGTCAG | 420 |
| TTTCCGTCAC | CGGAGCTCCT | CCGCCTCACT | ATGATTCCTT | GTCGAGCGAA | AACAGGAGCA | 480 |
| ACCATAACAG | CGGGAACACC | GGGAAAGCTA | AGGCGGAGAG | AGGCGGATTT | GATTGGGATC | 540 |
| CTAGCGGTGG | TGGTGGTGGT | GATCATAGGT | TGAATAATCA | ACCGAATCGG | GTTGGGAATA | 600 |
| ATATGTATGC | TTCGTCTCTA | GGGTTGCAAA | GGCAATCCAG | TGGGAGTAGT | TTCGGTGAGA | 660 |
| GCTCTTTGTC | TGGGGATTAT | TACATGCCTA | CGCTTTCTGC | GGCGGCTAAC | GAGATCGAAT | 720 |
| CTGTTGGATT | TCCTCAAGAT | GATGGGTTTA | GGCTTGGATT | TGGTGGTGGT | GGAGGAGATT | 780 |
| TGAGGATACA | GATGGCGGCG | GACTCCGCTG | GAGGGTCTTC | ATCTGGGAAG | AGCTGGGCGC | 840 |
| AGCAGACGGA | GGAGAGTTAT | CAGCTGCAGC | TTGCATTGGC | GTTAAGGCTT | TCGTCGGAGG | 900 |
| CTACTTGTGC | CGACGATCCG | AACTTTCTGG | ATCCTGTACC | GGACGAGTCT | GCTTTACGGA | 960 |
| CTTCGCCAAG | TTCAGCCGAA | ACCGTTTCAC | ATCGTTTCTG | GGTATTTGTT | CCTGTTAAGC | 1020 |
| TTTGTTTCCC | AAAATTATTG | AATCGTGGTT | ATAGAGATAT | GGTCCTCTTG | TTTCCGAAGT | 1080 |
| TTCAGTTAGA | TCTCCTTACC | AAAAGTCTAT | TAGTAGCAAA | TGAGATATGT | TGTTTAGATA | 1140 |
| CATTGCAGAG | TATGATTGTT | TTGTGTGCTG | CATCAGGTTA | ATGGCTGCTT | ATCGTACTAT | 1200 |
| GATAAAGTTC | CTGATGGGTT | TTATATGATG | AATGGTCTGG | ATCCCTATAT | TTGGACCTTA | 1260 |
| TGCATCGACC | TGCATGAAAG | TGGTCGCATC | CCTTCAATTG | AATCATTAAG | AGCTGTTGAT | 1320 |
| TCTGGTGTTG | ATTCTTCGCT | TGAAGCGATC | ATAGTTGATA | GGCGTAGTGA | TCCAGCCTTC | 1380 |
| AAGGAACTTC | ACAATAGAGT | CCACGACATA | TCTTGTAGCT | GCATTACCAC | AAAAGAGGTT | 1440 |
| GTTGATCAGC | TGGCAAAGCT | TATCTGCAAT | CGTATGGGGT | TGTACTCAT | ACAATCCTTA | 1500 |
| CTATCCCTTT | GAACTTATAT | TTTTATATCT | TCCTGTGATT | TCTCACATTG | TACTCGTTAA | 1560 |
| TTCTTGCTTC | CCCAGGGGTC | CAGTTATCAT | GGGGAAGAT | GAGTTGGTTC | CCATGTGGAA | 1620 |

| | | | | | |
|---|---|---|---|---|---|
| GGAGTGCATT | GATGGTCTAA | AAGAAATCTT | TAAAGTGGTG | GTTCCCATAG | GTAGCCTCTC | 1680
| TGTTGGACTC | TGCAGACATC | GAGCTTTACT | CTTCAAAGTG | AGATCCCAAC | TTTGATGCTA | 1740
| TCCCCATGAC | ATTTAAGACA | TCTTGTGAAA | TGATCATATA | AATTATTGTG | CTTCATCCAT | 1800
| TTGTTTTTAT | TGGAATACAT | ATGAAGAACG | TTGAATGTGA | AAAGTGGTGT | TATTGATTAG | 1860
| AAAAAAATAG | GTTACTGATA | GTTGAATGTT | CCAAGAAAA | AAAGTATTTT | ATATCTTCTA | 1920
| TTTGGTGCAT | GCAGGTACTG | GCTGACATAA | TTGATTTACC | CTGTCGAATT | GCCAAGGAT | 1980
| GTAAATATTG | TAATAGAGAC | GATGCCGCTT | CGTGCCTTGT | CAGGTTTGGG | CTTGATAGGT | 2040
| ATGATACAAG | TGATTGCGAA | AGAGCCTTTA | TTTTCCTATT | TTCTTTGCTT | TTTGTTTCTG | 2100
| GAAAAACAAT | TATAGCTCCA | AATGTTTCGC | AGAATATTAG | GTTGATGACG | TGGAAAATTT | 2160
| GTTTTGGTTT | CAGGGAGTAC | CTGGTTGATT | TAGTAGGAAA | GCCAGGTCAC | TTATGGGAGC | 2220
| CTGATTCCTT | GCTAAATGGT | CCTTCATCTA | TCTCAATTTC | TTCTCCTCTG | CGGTTCCAC | 2280
| GACCAAAGCC | AGTTGAACCC | GCAGTCGATT | TTAGGTTACT | AGCCAAACAA | TATTTCTCCG | 2340
| ATAGCCAGTC | TCTTAATCTT | GTTTTCGATC | CTGCATCAGG | TATTCCCATA | CAAAAAACCT | 2400
| GAATAATATG | TTAACTTTTT | GCATGCTGCT | TACATCTCGT | TTTGTATTTC | CCCTAAAAGA | 2460
| GTAATCTCCT | ATCATTTAGG | GTATTTCTTG | ATCATGTCTC | AGTATCTGAA | GTGTTAGTAG | 2520
| TCTTAGAATG | ATTCTATTGT | TTGTTTTCTT | GTCTCTTTTC | ACTTTAGTTG | TTTTTGGCTG | 2580
| TTGATGTGTA | TGTTTGTTGG | TGGGTTCTTT | GCCTAATGAT | ATTTAAGGTT | AAACTTGTTA | 2640
| GTCTGCTGTT | CAAGCTTATG | AATTCTAGTG | CATTTATGTG | CAAGACTTGT | CTTCTGGACT | 2700
| CTAATTTCTT | ATATCTGCTT | GTTTGAATGG | TTGTAGATGA | TATGGGATTC | TCAATGTTTC | 2760
| ATAGGCAATA | TGATAATCCG | GGTGGAGAGA | ATGACGCATT | GGCAGAAAAT | GGTGGTGGGT | 2820
| CTTTGCCACC | CAGTGCTAAT | ATGCCTCCAC | AGAACATGAT | GCGTGCGTCA | AATCAAATTG | 2880
| AAGCAGCACC | TATGAATGCC | CCACCAATCA | GTCAGCCAGT | TCCAAACAGG | GCAAATAGGG | 2940
| AACTTGGACT | TGATGGTGAT | GATATGGACA | TCCCGTGGTG | TGATCTTAAT | ATAAAGAAA | 3000
| AGATTGGAGC | AGGTAATAAT | TTTACGGAAA | AATTAATGAT | TCGGTCTAAA | AATGCAAAGA | 3060
| AATATGAAAT | TCTTGAGGAA | GTGGTTTTGC | TTTGGACTCT | GTTCTCGAAC | AAAATAAGGA | 3120
| AAAAGTGCCA | CCCATTTTGA | GATTACATTC | TTCTCTGTTG | CCTTTAATTC | TTCCACTCTA | 3180
| ATTTGAGCGA | CTGCTCTTTC | AGGTTCCTTT | GGCACTGTCC | ACCGTGCTGA | GTGGCATGGC | 3240
| TCGGTAAGAA | CTTTTTTGTC | AGAATTTACG | CAGCTGAATT | TTTTTTCGCT | CTAAAAATTT | 3300
| GGTTGTGACT | TTTGGATCTG | CTTGGTATTA | TAAAAGGCAA | AGTTATTGTA | TATGTGACTC | 3360
| TCCGTTCTGT | CAGAAATTAA | ACACGGACAA | AAGGTGTCCC | ATTTAGATG | TATATGTGTC | 3420
| TTTATATCAT | AAATTTGTCT | TCCTGTTTGA | ATTTACAAT | TCTATCACTA | GAAGAATTCT | 3480
| AATTTTGATT | ATTGCAGTAA | TATTCTCTAT | CAATTTCAGG | ATGTTGCTGT | GAAAATTCTC | 3540
| ATGGAGCAAG | ACTTCCATGC | TGAGCGTGTT | AATGAGTTCT | TAAGAGAGGT | GCACAAATAA | 3600
| AATTTCTCT | TGATTTGGT | AATGAACTTG | TTGTATTAAT | GTCTCCAATG | ATCTTGATTC | 3660
| GCTGTCAGGT | TGCGATAATG | AAACGCCTTC | GCCACCCTAA | CATTGTTCTC | TTCATGGGTG | 3720
| CGGTCACTCA | ACCTCCAAAT | TTGTCAATAG | TGACAGAATA | TTTGTCAAGG | TACAATTACT | 3780
| TGGATTTGGA | AGGTTTGATG | TACTGAGTGT | AGAATTTTGG | CCTATAATGA | CTCTAATACC | 3840
| ATGATTTCTT | TCAAACAGAG | GTAGTTTATA | CAGACTTTTG | CATAAAAGTG | GAGCAAGGGA | 3900
| GCAATTAGAT | GAGAGACGTC | GCCTGAGTAT | GGCTTATGAT | GTGGTATGTT | TAACTCCTTA | 3960
| TGTTACATGT | ATGGGTGATT | ACTTCCTGAT | CTTGGTGTTT | CTTCACATGG | AACTTTCTTT | 4020
| CCAATTCTCT | GTCACAGGCT | AAGGGAATGA | ATTATCTTCA | CAATCGCAAT | CCTCCAATTG | 4080

| | | | | | |
|---|---|---|---|---|---|
| TGCATAGAGA | TCTAAAATCT | CCAAACTTAT | TGGTTGACAA | AAAATATACA | GTCAAGGTTT | 4140
| GAATCTAAAT | TAGAAATTGT | TGTGTCCAAT | GTTTTGATTT | TGATATTTTA | TTCCTCTTGT | 4200
| GAGACAAGCT | TATATATAAA | TTATGATTTT | TAATTCTAAA | TTGGTTTGGA | GACATTACAA | 4260
| AAAGGCGTTA | ATCTGCTGAA | ACTTAAAAGA | TACAGCAGCC | TCAAGCTGTC | GTCTTAAAAA | 4320
| CAATCAGAAC | ATTATTATTC | TAACTCCTCA | ATTTGTCTTG | AAATTTCAGG | TTTGTGATTT | 4380
| TGGTCTCTCG | CGATTGAAGG | CCAGCACGTT | TCTTTCCTCG | AAGTCAGCAG | CTGGAACCGT | 4440
| AAGTTCAGTT | TGTTTGAAAC | TAAAACACGC | TGAACAACGT | AACTTTCTTC | TAGGTCCTAT | 4500
| TTCCAATGGA | AGCTAAATAA | TTACTGACTT | TGATATATCA | GCCCGAGTGG | ATGGCACCAG | 4560
| AAGTCCTGCG | AGATGAGCCG | TCTAATGAAA | AGTCAGATGT | GTACAGCTTC | GGGGTCATCT | 4620
| TGTGGGAGCT | TGCTACATTG | CAACAACCAT | GGGGTAACTT | AAATCCGGCT | CAGGTACTTC | 4680
| CCACTCTAAA | CATCCCAAAT | AATAATGATA | TTATTTTGCA | TTTGGAAGTC | CCTCACTCTA | 4740
| CATTTCATAA | CATGCTATAT | ATGATCATCC | AACAAATGT | TCCATAGGTT | GTAGCTGCGG | 4800
| TTGGTTTCAA | GTGTAAACGG | CTGGAGATCC | CGCGTAATCT | GAATCCTCAG | GTTGCAGCCA | 4860
| TAATCGAGGG | TTGTTGGACC | AAGTACGTTA | AGATTTTCTA | TCTCTTTTTT | GAATTCTTCT | 4920
| TGAATAGACT | TCATGTTTAT | GTATGTGTTT | CATTACCAGT | GAGCCATGGA | AGCGTCCATC | 4980
| ATTTGCAACT | ATAATGGACT | TGCTAAGACC | ATTGATCAAA | TCAGCGGTTC | CTCCGCCCAA | 5040
| CCGCTCGGAT | TTGTAAAATA | CCCCCGGTCC | ATTCAAAGT | TGTTATAATC | ATGATATGCA | 5100
| CATATACTCT | CAGCATTCTT | TTGCTGCCCA | GGAGGGAGAC | ACTAGTTAAG | ATATAGCTTT | 5160
| AAAGGTACAT | TCCTCATGAG | CTATCAATCA | TATCCTACAG | AATCCCATGG | TTTTTATACA | 5220
| TGTATTATTT | TTGCGATCTT | TGTCTGCTGT | TTTGTTCCCT | TTTTAATGTT | GCAGATTGTT | 5280
| AAAATGTACA | TGACTATTGT | CACAGGGAGG | AAAAAAAAAT | GTAGTAATGG | AAACAATGTG | 5340
| AGGGATATAA | TCTATCTATC | TAGTCCCAAA | GGGTAAGCAA | TATTGTGTTG | TTATGTCTTT | 5400
| GTAGCAATGC | ACTGAAAGCT | ATATTTAATT | ACATTGCTGT | ACATTTATAC | CGCTAAATTA | 5460
| GTTACTAAGC | GAAGGTAAAA | AAGAGCAGCT | GGTAAATGCT | GTCAAAGGGT | TTTGCAAACT | 5520
| CAATATGATT | CATTGGATTT | ACATTTGTTC | ACTGTGCGAT | TAGTCTGGAC | TATAAACCAA | 5580
| CAGAAATGAA | ATAAGACTGT | AACTTTCGGA | GACTCTAATA | CAGATGAATA | TAATCCCAAA | 5640
| TCGTTAAAAA | CGCATTGGGA | CTGAAAATAT | CTAGATACAT | AGTCAACTAT | TTTTGCCTTC | 5700
| GCGTCTAAGT | AAGTTCCCAC | ACTTGAAAAC | GACTTACCT | GTCTTCCGAA | TTAATCGTTT | 5760
| GATGGATCGG | TAACCAATAG | GATTGCGTAA | ATCAAAATTA | TACAATATTA | AATTCTGAAA | 5820
| AAGGAAACAC | GAAAAGCGAA | TCAGTGATTT | GTGAGGGCCC | AGTTCCAAAT | TAGAAAGCTG | 5880
| ACCTGGCAAA | | | | | | 5890

( 2 ) INFORMATION FOR SEQ ID NO:4:

( i ) SEQUENCE CHARACTERISTICS:
        ( A ) LENGTH: 5873 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| | | | | | |
|---|---|---|---|---|---|
| GCACACTAAA | TTGAGAATT | GTTTTGACCC | AAAATAAAAA | AAATGTCAAA | GTTCCATAAA | 60
| GAAGGAGGAC | ACAAGAGGAA | TATAACGAAA | TTATCAACAG | AGACGCACCG | AGTAAGTTTA | 120
| TTTCCTATGA | TAACGCCCAA | ACACAAAAAA | AATCCAATTC | CATTAGAGAG | AGAGAGAGAG | 180
| AGAGAGAGAG | AGAGAGACTT | TTTAGAAAG | TACACAAAAA | AAATGAAAAA | CTAGAGAGAG | 240

```
AAACAAGTGG CTAGCTAGCT CGCCAAACTT CTTCAACAAT GGCGGTTTCC TAGGGTTTGA    300
TGTTTATATG ATCGGGAAAC TCTCTCATCT AGATCGCGAT AACTCTCTTT TCCATGGAAA    360
TGCCCGGTAG AAGATCTAAT TACACTTTGC TTAGTCAATT TTCTGACGAT CAGGTGTCAG    420
TTTCCGTCAC CGGAGCTCCT CCGCCTCACT ATGATTCCTT GTCGAGCGAA AACAGGAGCA    480
ACCATAACAG CGGGAACACC GGGAAAGCTA AGGCGGAGAG AGGCGGATTT GATTGGGATC    540
CTAGCGGTGG TGGTGGTGGT GATCATAGGT TGAATAATCA ACCGAATCGG GTTGGGAATA    600
ATATGTATGC TTCGTCTCTA GGGTTGCAAA GGCAATCCAG TGGGAGTAGT TTCGGTGAGA    660
GCTCTTTGTC TGGGATTAT TACATGCCTA CGCTTTCTGC GGCGGCTAAC GAGATCGAAT     720
CTGTTGGATT TCCTCAAGAT GATGGGTTTA GGCTTGGATT TGGTGGTGGT GGAGGAGATT    780
TGAGGATACA GATGGCGGCG GACTCCGCTG GAGGGTCTTC ATCTGGGAAG AGCTGGGCGC    840
AGCAGACGGA GGAGAGTTAT CAGCTGCAGC TTGCATTGGC GTTAAGGCTT TCGTCGGAGG    900
CTACTTGTGC CGACGATCCG AACTTTCTGG ATCCTGTACC GGACGAGTCT GCTTTACGGA    960
CTTCGCCAAG TTCAGCCGAA ACCGTTTCAC ATCGTTTCTG GTATTTGTT CCTGTTAAGC    1020
TTTGTTTCCC AAAATTATTG AATCGTGGTT ATAGAGATAT GGTCCTCTTG TTTCCGAAGT   1080
TTCAGTTAGA TCTCCTTACC AAAAGTCTAT TAGTAGCAAA TGAGATATGT TGTTTAGATA   1140
CATTGCAGAG TATGATTGTT TTGTGTGCTG CATCAGGTTA ATGGCTGCTT ATCGTACTAT   1200
GATAAAGTTC CTGATGGGTT TTATATGATG AATGGTCTGG ATCCCTATAT TTGGACCTTA   1260
TGCATCGACC TGCATGAAAG TGGTCGCATC CCTTCAATTG AATCATTAAG AGCTGTTGAT   1320
TCTGGTGTTG ATTCTTCGCT TGAAGCGATC ATAGTTGATA GGCGTAGTGA TCCAGCCTTC   1380
AAGGAACTTC ACAATAGAGT CCACGACATA TCTTGTAGCT GCATTACCAC AAAAGAGGTT   1440
GTTGATCAGC TGGCAAAGCT TATCTGCAAT CGTATGGGGT TTGTACTCAT ACAATCCTTA   1500
CTATCCCTTT GAACTTATAT TTTTATATCT TCCTGTGATT TCTCACATTG TACTCGTTAA   1560
TTCTTGCTTC CCCAGGGGTC CAGTTATCAT GGGGAAGAT GAGTTGGTTC CCATGTGGAA    1620
GGAGTGCATT GATGGTCTAA AAGAAATCTT TAAAGTGGTG GTTCCCATAG GTAGCCTCTC   1680
TGTTGGACTC TGCAGACATC GAGCTTTACT CTTCAAAGTG AGATCCCAAC TTTGATGCTA   1740
TCCCCATGAC ATTTAAGACA TCTTGTGAAA TGATCATATA AATTATTGTG CTTCATCCAT   1800
TTGTTTTTAT TGGAATACAT ATGAAGAACG TTGAATGTGA AAAGTGGTGT TATTGATTAG   1860
AAAAAAATAG GTTACTGATA GTTGAATGTT CCAAAGAAAA AAAGTATTTT ATATCTTCTA   1920
TTTGGTGCAT GCAGGTACTG GCTGACATAA TTGATTTACC CTGTCGAATT GCCAAAGGAT   1980
GTAAATATTG TAATAGAGAC GATGCCGCTT CGTGCCTTGT CAGGTTTGGG CTTGATAGGT   2040
ATGATACAAG TGATTGCGAA AGAGCCTTTA TTTTCCTATT TTCTTTGCTT TTTGTTTCTG   2100
GAAAACAAT TATAGCTCCA AATGTTTCGC AGAATATTAG GTTGATGACG TGGAAAATTT    2160
GTTTTGGTTT CAGGGAGTAC CTGGTTGATT TAGTAGGAAA GCCAGGTCAC TTATGGGAGC   2220
CTGATTCCTT GCTAAATGGT CCTTCATCTA TCTCAATTTC TTCTCCTCTG CGGTTCCAC    2280
GACCAAAGCC AGTTGAACCC GCAGTCGATT TTAGGTTACT AGCCAAACAA TATTTCTCCG   2340
ATAGCCATCG ATCCTGCATC AGGTATTCCC ATACAAAAAA CCTGAATAAT ATGTTAACTT   2400
TTTGCATGCT GCTTACATCT CGTTTTGTAT TTCCCCTAAA AGAGTAATCT CCTATCATTT   2460
AGGGTATTTC TTGATCATGT CTCAGTATCT GAAGTGTTAG TAGTCTTAGA ATGATTCTAT   2520
TGTTTGTTTT CTTGTCTCTT TTCACTTTAG TTGTTTTTGG CTGTTGATGT GTATGTTTGT   2580
TGGTGGGTTC TTTGCCTAAT GATATTTAAG GTTAAACTTG TTAGTCTGCT GTTCAAGCTT   2640
ATGAATTCTA GTGCATTTAT GTGCAAGACT TGTCTTCTGG ACTCTAATTT CTTATATCTG   2700
```

| | | | | | |
|---|---|---|---|---|---|
|CTTGTTTGAA|TGGTTGTAGA|TGATATGGGA|TTCTCAATGT|TTCATAGGCA|ATATGATAAT|2760|
|CCGGGTGGAG|AGAATGACGC|ATTGGCAGAA|AATGGTGGTG|GGTCTTGCC|ACCCAGTGCT|2820|
|AATATGCCTC|CACAGAACAT|GATGCGTGCG|TCAAATCAAA|TTGAAGCAGC|ACCTATGAAT|2880|
|GCCCCACCAA|TCAGTCAGCC|AGTTCCAAAC|AGGGCAAATA|GGGAACTTGG|ACTTGATGGT|2940|
|GATGATATGG|ACATCCCGTG|GTGTGATCTT|AATATAAAAG|AAAGATTGG|AGCAGGTAAT|3000|
|AATTTTACGG|AAAAATTAAT|GATTCGGTCT|AAAAATGCAA|AGAAATATGA|AATTCTTGAG|3060|
|GAAGTGGTTT|TGCTTTGGAC|TCTGTTCTCG|AACAAATAA|GGAAAAGTG|CCACCCATTT|3120|
|TGAGATTACA|TTCTTCTCTG|TTGCCTTTAA|TTCTTCCACT|CTAATTGAG|CGACTGCTCT|3180|
|TTCAGGTTCC|TTTGGCACTG|TCCACCGTGC|TGAGTGGCAT|GGCTCGGTAA|GAACTTTTT|3240|
|GTCAGAATTT|ACGCAGCTGA|ATTTTTTTC|GCTCTAAAAA|TTTGGTTGTG|ACTTTGGAT|3300|
|CTGCTTGGTA|TTATAAAAGG|CAAAGTTATT|GTATATGTGA|CTCTCCGTTC|TGTCAGAAAT|3360|
|TAAACACGGA|CAAAAGGTGT|CCCATTTTAG|ATGTATATGT|GTCTTTATAT|CATAAATTTG|3420|
|TCTTCCTGTT|TGAATTTTAC|AATTCTATCA|CTAGAAGAAT|TCTAATTTG|ATTATTGCAG|3480|
|TAATATTCTC|TATCAATTTC|AGGATGTTGC|TGTGAAAATT|CTCATGGAGC|AAGACTTCCA|3540|
|TGCTGAGCGT|GTTAATGAGT|TCTTAAGAGA|GGTGCACAAA|TAAAATTTTC|TCTTGATTTT|3600|
|GGTAATGAAC|TTGTTGTATT|AATGTCTCCA|ATGATCTTGA|TTCGCTGTCA|GGTTGCGATA|3660|
|ATGAAACGCC|TTCGCCACCC|TAACATTGTT|CTCTTCATGG|GTGCGGTCAC|TCAACCTCCA|3720|
|AATTTGTCAA|TAGTGACAGA|ATATTTGTCA|AGGTACAATT|ACTTGGATTT|GGAAGGTTTG|3780|
|ATGTACTGAG|TGTAGAATTT|TGGCCTATAA|TGACTCTAAT|ACCATGATTT|CTTTCAAACA|3840|
|GAGGTAGTTT|ATACAGACTT|TTGCATAAAA|GTGGAGCAAG|GGAGCAATTA|GATGAGAGAC|3900|
|GTCGCCTGAG|TATGGCTTAT|GATGTGGTAT|GTTAACTCC|TTATGTTACA|TGTATGGGTG|3960|
|ATTACTTCCT|GATCTTGGTG|TTTCTTCACA|TGGAACTTTC|TTTCCAATTC|TCTGTCACAG|4020|
|GCTAAGGGAA|TGAATTATCT|TCACAATCGC|AATCCTCCAA|TTGTGCATAG|AGATCTAAAA|4080|
|TCTCCAAACT|TATTGGTTGA|CAAAAAATAT|ACAGTCAAGG|TTTGAATCTA|AATTAGAAAT|4140|
|TGTTGTGTCC|AATGTTTTGA|TTTTGATATT|TTATTCCTCT|TGTGAGACAA|GCTTATATAT|4200|
|AAATTATGAT|TTTTAATTCT|AAATTGGTTT|GGAGACATTA|CAAAAAGGCG|TTAATCTGCT|4260|
|GAAACTTAAA|AGATACAGCA|GCCTCAAGCT|GTCGTCTTAA|AAACAATCAG|AACATTATTA|4320|
|TTCTAACTCC|TCAATTTGTC|TTGAAATTTC|AGGTTTGTGA|TTTTGGTCTC|TCGCGATTGA|4380|
|AGGCCAGCAC|GTTTCTTTCC|TCGAAGTCAG|CAGCTGGAAC|CGTAAGTTCA|GTTTGTTTGA|4440|
|AACTAAAACA|CGCTGAACAA|CGTAACTTTC|TTCTAGGTCC|TATTTCCAAT|GGAAGCTAAA|4500|
|TAATTACTGA|CTTTGATATA|TCAGCCCGAG|TGGATGGCAC|CAGAAGTCCT|GCGAGATGAG|4560|
|CCGTCTAATG|AAAAGTCAGA|TGTGTACAGC|TTCGGGGTCA|TCTTGTGGGA|GCTTGCTACA|4620|
|TTGCAACAAC|CATGGGGTAA|CTTAAATCCG|GCTCAGGTAC|TTCCCACTCT|AAACATCCCA|4680|
|AATAATAATG|ATATTATTTT|GCATTTGGAA|GTCCCTCACT|CTACATTTCA|TAACATGCTA|4740|
|TATATGATCA|TCCAACAAAA|TGTTCCATAG|GTTGTAGCTG|CGGTTGGTTT|CAAGTGTAAA|4800|
|CGGCTGGAGA|TCCCGCGTAA|TCTGAATCCT|CAGGTTGCAG|CCATAATCGA|GGGTTGTTGG|4860|
|ACCAAGTACG|TTAAGATTTT|CTATCTCTTT|TTTGAATTCT|TCTTGAATAG|ACTTCATGTT|4920|
|TATGTATGTG|TTTCATTACC|AGTGAGCCAT|GGAAGCGTCC|ATCATTTGCA|ACTATAATGG|4980|
|ACTTGCTAAG|ACCATTGATC|AAATCAGCGG|TTCCTCCGCC|CAACCGCTCG|GATTTGTAAA|5040|
|ATACCCCCGG|TCCATTCAAA|AGTTGTTATA|ATCATGATAT|GCACATATAC|TCTCAGCATT|5100|
|CTTTTGCTGC|CCAGGAGGGA|GACACTAGTT|AAGATATAGC|TTTAAGGTA|CATTCCTCAT|5160|

-continued

```
GAGCTATCAA TCATATCCTA CAGAATCCCA TGGTTTTTAT ACATGTATTA TTTTTGCGAT    5220
CTTTGTCTGC TGTTTTGTTC CCTTTTAAT GTTGCAGATT GTTAAAATGT ACATGACTAT    5280
TGTCACAGGG AGGAAAAAAA AATGTAGTAA TGGAAACAAT GTGAGGGATA TAATCTATCT    5340
ATCTAGTCCC AAAGGGTAAG CAATATTGTG TTGTTATGTC TTTGTAGCAA TGCACTGAAA    5400
GCTATATTTA ATTACATTGC TGTACATTTA TACCGCTAAA TTAGTTACTA AGCGAAGGTA    5460
AAAAAGAGCA GCTGGTAAAT GCTGTCAAAG GGTTTTGCAA ACTCAATATG ATTCATTGGA    5520
TTTACATTTG TTCACTGTGC GATTAGTCTG GACTATAAAC CAACAGAAAT GAAATAAGAC    5580
TGTAACTTTC GGAGACTCTA ATACAGATGA ATATAATCCC AAATCGTTAA AAACGCATTG    5640
GGACTGAAAA TATCTAGATA CATAGTCAAC TATTTTGCC TTCGCGTCTA AGTAAGTTCC    5700
CACACTTGAA AACGACTTTA CCTGTCTTCC GAATTAATCG TTTGATGGAT CGGTAACCAA    5760
TAGGATTGCG TAAATCAAAA TTATACAATA TTAAATTCTG AAAAAGGAAA CACGAAAAGC    5820
GAATCAGTGA TTTGTGAGGG CCCAGTTCCA AATTAGAAAG CTGACCTGGC AAA          5873
```

(2) INFORMATION FOR SEQ ID NO:5:

(i) SEQUENCE CHARACTERISTICS:
        (A) LENGTH: 5890 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GCACACTAAA TTGGAGAATT GTTTTGACCC AAAATAAAAA AAATGTCAAA GTTCCATAAA      60
GAAGGAGGAC ACAAGAGGAA TATAACGAAA TTATCAACAG AGACGCACCG AGTAAGTTTA     120
TTTCCTATGA TAACGCCCAA ACACAAAAAA AATCCAATTC CATTAGAGAG AGAGAGAGAG     180
AGAGAGAGAG AGAGAGACTT TTTTAGAAAG TACACAAAAA AAATGAAAAA CTAGAGAGAG     240
AAACAAGTGG CTAGCTAGCT CGCCAAACTT CTTCAACAAT GGCGGTTTCC TAGGGTTTGA     300
TGTTTATATG ATCGGGAAAC TCTCTCATCT AGATCGCGAT AACTCTCTTT TCCATGGAAA     360
TGCCCGGTAG AAGATCTAAT TACACTTTGC TTAGTCAATT TTCTGACGAT CAGGTGTCAG     420
TTTCCGTCAC CGGAGCTCCT CCGCCTCACT ATGATTCCTT GTCGAGCGAA AACAGGAGCA     480
ACCATAACAG CGGGAACACC GGGAAAGCTA AGGCGGAGAG AGGCGGATTT GATTGGGATC     540
CTAGCGGTGG TGGTGGTGGT GATCATAGGT TGAATAATCA ACCGAATCGG GTTGGGAATA     600
ATATGTATGC TTCGTCTCTA GGGTTGCAAA GGCAATCCAG TGGGAGTAGT TTCGGTGAGA     660
GCTCTTTGTC TGGGGATTAT TACATGCCTA CGCTTTCTGC GGCGGCTAAC GAGATCGAAT     720
CTGTTGGATT TCCTCAAGAT GATGGGTTTA GGCTTGGATT TGGTGGTGGT GGAGGAGATT     780
TGAGGATACA GATGGCGGCG GACTCCGCTG GAGGGTCTTC ATCTGGGAAG AGCTGGGCGC     840
AGCAGACGGA GGAGAGTTAT CAGCTGCAGC TTGCATTGGC GTTAAGGCTT CGTCGGAGG     900
CTACTTGTGC CGACGATCCG AACTTTCTGG ATCCTGTACC GGACGAGTCT GCTTTACGGA     960
CTTCGCCAAG TTCAGCCGAA ACCGTTTCAC ATCGTTTCTG GGTATTTGTT CCTGTTAAGC    1020
TTTGTTTCCC AAAATTATTG AATCGTGGTT ATAGAGATAT GGTCCTCTTG TTTCCGAAGT    1080
TTCAGTTAGA TCTCCTTACC AAAAGTCTAT TAGTAGCAAA TGAGATATGT TGTTTAGATA    1140
CATTGCAGAG TATGATTGTT TTGTGTGCTG CATCAGGTTA ATGGCTGCTT ATCGTACTAT    1200
GATAAAGTTC CTGATGGGTT TTATATGATG AATGGTCTGG ATCCCTATAT TTGGACCTTA    1260
TGCATCGACC TGCATGAAAG TGGTCGCATC CCTTCAATTG AATCATTAAG AGCTGTTGAT    1320
```

```
TCTGGTGTTG ATTCTTCGCT TGAAGCGATC ATAGTTGATA GGCGTAGTGA TCCAGCCTTC       1380
AAGGAACTTC ACAATAGAGT CCACGACATA TCTTGTAGCT GCATTACCAC AAAAGAGGTT       1440
GTTGATCAGC TGGCAAAGCT TATCTGCAAT CGTATGGGGT TTGTACTCAT ACAATCCTTA       1500
CTATCCCTTT GAACTTATAT TTTTATATCT TCCTGTGATT CTCACATTG TACTCGTTAA        1560
TTCTTGCTTC CCCAGGGGTC CAGTTATCAT GGGGGAAGAT GAGTTGGTTC CCATGTGGAA       1620
GGAGTGCATT GATGGTCTAA AGAAATCTT TAAAGTGGTG GTTCCCATAG GTAGCCTCTC        1680
TGTTGGACTC TGCAGACATC GAGCTTTACT CTTCAAAGTG AGATCCCAAC TTTGATGCTA       1740
TCCCCATGAC ATTTAAGACA TCTTGTGAAA TGATCATATA AATTATTGTG CTTCATCCAT       1800
TTGTTTTTAT TGGAATACAT ATGAAGAACG TTGAATGTGA AAAGTGGTGT TATTGATTAG       1860
AAAAAAATAG GTTACTGATA GTTGAATGTT CCAAGAAAA AAAGTATTTT ATATCTTCTA        1920
TTTGGTGCAT GCAGGTACTG GCTGACATAA TTGATTTACC CTGTCGAATT GCCAAAGGAT       1980
GTAAATATTG TAATAGAGAC GATGCCGCTT CGTGCCTTGT CAGGTTTGGG CTTGATAGGT       2040
ATGATACAAG TGATTGCGAA AGAGCCTTTA TTTTCCTATT TTCTTTGCTT TTTGTTTCTG       2100
GAAAAACAAT TATAGCTCCA AATGTTTCGC AGAATATTAG GTTGATGACG TGGAAAATTT       2160
GTTTTGGTTT CAGGGAGTAC CTGGTTGATT TAGTAGGAAA GCCAGGTCAC TTATGGGAGC       2220
CTGATTCCTT GCTAAATGGT CCTTCATCTA TCTCAATTTC TTCTCCTCTG CGGTTTCCAT       2280
GACCAAAGCC AGTTGAACCC GCAGTCGATT TTAGGTTACT AGCCAAACAA TATTTCTCCG       2340
ATAGCCAGTC TCTTAATCTT GTTTTCGATC CTGCATCAGG TATTCCCATA CAAAAAACCT       2400
GAATAATATG TTAACTTTTT GCATGCTGCT TACATCTCGT TTTGTATTTC CCCTAAAAGA       2460
GTAATCTCCT ATCATTTAGG GTATTTCTTG ATCATGTCTC AGTATCTGAA GTGTTAGTAG       2520
TCTTAGAATG ATTCTATTGT TTGTTTTCTT GTCTCTTTTC ACTTTAGTTG TTTTTGGCTG       2580
TTGATGTGTA TGTTTGTTGG TGGGTTCTTT GCCTAATGAT ATTTAAGGTT AAACTTGTTA       2640
GTCTGCTGTT CAAGCTTATG AATTCTAGTG CATTTATGTG CAAGACTTGT CTTCTGGACT       2700
CTAATTTCTT ATATCTGCTT GTTTGAATGG TTGTAGATGA TATGGGATTC TCAATGTTTC       2760
ATAGGCAATA TGATAATCCG GGTGGAGAGA ATGACGCATT GGCAGAAAAT GGTGGTGGGT       2820
CTTTGCCACC CAGTGCTAAT ATGCCTCCAC AGAACATGAT GCGTGCGTCA ATCAAATTG        2880
AAGCAGCACC TATGAATGCC CCACCAATCA GTCAGCCAGT TCCAAACAGG GCAAATAGGG       2940
AACTTGGACT TGATGGTGAT GATATGGACA TCCCGTGGTG TGATCTTAAT ATAAAAGAAA       3000
AGATTGGAGC AGGTAATAAT TTTACGGAAA AATTAATGAT TCGGTCTAAA AATGCAAAGA       3060
AATATGAAAT TCTTGAGGAA GTGGTTTTGC TTTGGACTCT GTTCTCGAAC AAAATAAGGA       3120
AAAAGTGCCA CCCATTTTGA GATTACATTC TTCTCTGTTG CCTTTAATTC TTCCACTCTA       3180
ATTTGAGCGA CTGCTCTTTC AGGTTCCTTT GGCACTGTCC ACCGTGCTGA GTGGCATGGC       3240
TCGGTAAGAA CTTTTTTGTC AGAATTTACG CAGCTGAATT TTTTTCGCT CTAAAAATTT        3300
GGTTGTGACT TTTGGATCTG CTTGGTATTA TAAAAGGCAA AGTTATTGTA TATGTGACTC       3360
TCCGTTCTGT CAGAAATTAA ACACGGACAA AAGGTGTCCC ATTTAGATG TATATGTGTC        3420
TTTATATCAT AAATTTGTCT TCCTGTTTGA ATTTACAAT TCTATCACTA GAAGAATTCT        3480
AATTTGATT ATTGCAGTAA TATTCTCTAT CAATTTCAGG ATGTTGCTGT GAAAATTCTC        3540
ATGGAGCAAG ACTTCCATGC TGAGCGTGTT AATGAGTTCT TAAGAGAGGT GCACAAATAA       3600
AATTTCTCT TGATTTGGT AATGAACTTG TTGTATTAAT GTCTCCAATG ATCTTGATTC         3660
GCTGTCAGGT TGCGATAATG AAACGCCTTC GCCACCCTAA CATTGTTCTC TTCATGGGTG       3720
CGGTCACTCA ACCTCCAAAT TTGTCAATAG TGACAGAATA TTTGTCAAGG TACAATTACT       3780
```

```
TGGATTTGGA  AGGTTTGATG  TACTGAGTGT  AGAATTTTGG  CCTATAATGA  CTCTAATACC   3840
ATGATTTCTT  TCAAACAGAG  GTAGTTTATA  CAGACTTTTG  CATAAAAGTG  GAGCAAGGGA   3900
GCAATTAGAT  GAGAGACGTC  GCCTGAGTAT  GGCTTATGAT  GTGGTATGTT  TAACTCCTTA   3960
TGTTACATGT  ATGGGTGATT  ACTTCCTGAT  CTTGGTGTTT  CTTCACATGG  AACTTTCTTT   4020
CCAATTCTCT  GTCACAGGCT  AAGGGAATGA  ATTATCTTCA  CAATCGCAAT  CCTCCAATTG   4080
TGCATAGAGA  TCTAAAATCT  CCAAACTTAT  TGGTTGACAA  AAAATATACA  GTCAAGGTTT   4140
GAATCTAAAT  TAGAAATTGT  TGTGTCCAAT  GTTTGATTT   TGATATTTTA  TTCCTCTTGT   4200
GAGACAAGCT  TATATATAAA  TTATGATTTT  TAATTCTAAA  TTGGTTTGGA  GACATTACAA   4260
AAAGGCGTTA  ATCTGCTGAA  ACTTAAAAGA  TACAGCAGCC  TCAAGCTGTC  GTCTTAAAAA   4320
CAATCAGAAC  ATTATTATTC  TAACTCCTCA  ATTTGTCTTG  AAATTTCAGG  TTTGTGATTT   4380
TGGTCTCTCG  CGATTGAAGG  CCAGCACGTT  TCTTCCTCG   AAGTCAGCAG  CTGGAACCGT   4440
AAGTTCAGTT  TGTTTGAAAC  TAAAACACGC  TGAACAACGT  AACTTCTTC   TAGGTCCTAT   4500
TTCCAATGGA  AGCTAAATAA  TTACTGACTT  TGATATATCA  GCCCGAGTGG  ATGGCACCAG   4560
AAGTCCTGCG  AGATGAGCCG  TCTAATGAAA  AGTCAGATGT  GTACAGCTTC  GGGGTCATCT   4620
TGTGGGAGCT  TGCTACATTG  CAACAACCAT  GGGGTAACTT  AAATCCGGCT  CAGGTACTTC   4680
CCACTCTAAA  CATCCCAAAT  AATAATGATA  TTATTTGCA   TTTGGAAGTC  CCTCACTCTA   4740
CATTTCATAA  CATGCTATAT  ATGATCATCC  AACAAAATGT  TCCATAGGTT  GTAGCTGCGG   4800
TTGGTTTCAA  GTGTAAACGG  CTGGAGATCC  CGCGTAATCT  GAATCCTCAG  GTTGCAGCCA   4860
TAATCGAGGG  TTGTTGGACC  AAGTACGTTA  AGATTTTCTA  TCTCTTTTTT  GAATTCTTCT   4920
TGAATAGACT  TCATGTTTAT  GTATGTGTTT  CATTACCAGT  GAGCCATGGA  AGCGTCCATC   4980
ATTTGCAACT  ATAATGGACT  TGCTAAGACC  ATTGATCAAA  TCAGCGGTTC  CTCCGCCCAA   5040
CCGCTCGGAT  TTGTAAAATA  CCCCCGGTCC  ATTCAAAAGT  TGTTATAATC  ATGATATGCA   5100
CATATACTCT  CAGCATTCTT  TTGCTGCCCA  GGAGGGAGAC  ACTAGTTAAG  ATATAGCTTT   5160
AAAGGTACAT  TCCTCATGAG  CTATCAATCA  TATCCTACAG  AATCCCATGG  TTTTTATACA   5220
TGTATTATTT  TTGCGATCTT  TGTCTGCTGT  TTTGTTCCCT  TTTTAATGTT  GCAGATTGTT   5280
AAAATGTACA  TGACTATTGT  CACAGGGAGG  AAAAAAAAAT  GTAGTAATGG  AAACAATGTG   5340
AGGGATATAA  TCTATCTATC  TAGTCCCAAA  GGGTAAGCAA  TATTGTGTTG  TTATGTCTTT   5400
GTAGCAATGC  ACTGAAAGCT  ATATTTAATT  ACATTGCTGT  ACATTTATAC  CGCTAAATTA   5460
GTTACTAAGC  GAAGGTAAAA  AAGAGCAGCT  GGTAAATGCT  GTCAAAGGGT  TTTGCAAACT   5520
CAATATGATT  CATTGGATTT  ACATTTGTTC  ACTGTGCGAT  TAGTCTGGAC  TATAAACCAA   5580
CAGAAATGAA  ATAAGACTGT  AACTTTCGGA  GACTCTAATA  CAGATGAATA  TAATCCCAAA   5640
TCGTTAAAAA  CGCATTGGGA  CTGAAAATAT  CTAGATACAT  AGTCAACTAT  TTTTGCCTTC   5700
GCGTCTAAGT  AAGTTCCCAC  ACTTGAAAAC  GACTTTACCT  GTCTTCCGAA  TTAATCGTTT   5760
GATGGATCGG  TAACCAATAG  GATTGCGTAA  ATCAAAATTA  TACAATATTA  AATTCTGAAA   5820
AAGGAAACAC  GAAAAGCGAA  TCAGTGATTT  GTGAGGGCCC  AGTTCCAAAT  TAGAAAGCTG   5880
ACCTGGCAAA                                                              5890
```

( 2 ) INFORMATION FOR SEQ ID NO:6:

( i ) SEQUENCE CHARACTERISTICS:
        ( A ) LENGTH: 5890 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

| | | | | | | |
|---|---|---|---|---|---|---|
| GCACACTAAA | TTGGAGAATT | GTTTTGACCC | AAAATAAAAA | AAATGTCAAA | GTTCCATAAA | 60 |
| GAAGGAGGAC | ACAAGAGGAA | TATAACGAAA | TTATCAACAG | AGACGCACCG | AGTAAGTTTA | 120 |
| TTTCCTATGA | TAACGCCCAA | ACACAAAAAA | AATCCAATTC | CATTAGAGAG | AGAGAGAGAG | 180 |
| AGAGAGAGAG | AGAGAGACTT | TTTTAGAAAG | TACACAAAAA | AAATGAAAAA | CTAGAGAGAG | 240 |
| AAACAAGTGG | CTAGCTAGCT | CGCCAAACTT | CTTCAACAAT | GGCGGTTTCC | TAGGGTTTGA | 300 |
| TGTTTATATG | ATCGGGAAAC | TCTCTCATCT | AGATCGCGAT | AACTCTCTTT | TCCATGGAAA | 360 |
| TGCCCGGTAG | AAGATCTAAT | TACACTTTGC | TTAGTCAATT | TTCTGACGAT | CAGGTGTCAG | 420 |
| TTTCCGTCAC | CGGAGCTCCT | CCGCCTCACT | ATGATTCCTT | GTCGAGCGAA | AACAGGAGCA | 480 |
| ACCATAACAG | CGGGAACACC | GGGAAAGCTA | AGGCGGAGAG | AGGCGGATTT | GATTGGGATC | 540 |
| CTAGCGGTGG | TGGTGGTGGT | GATCATAGGT | TGAATAATCA | ACCGAATCGG | GTTGGGAATA | 600 |
| ATATGTATGC | TTCGTCTCTA | GGGTTGCAAA | GGCAATCCAG | TGGGAGTAGT | TTCGGTGAGA | 660 |
| GCTCTTTGTC | TGGGGATTAT | TACATGCCTA | CGCTTTCTGC | GGCGGCTAAC | GAGATCGAAT | 720 |
| CTGTTGGATT | TCCTCAAGAT | GATGGGTTTA | GGCTTGGATT | TGGTGGTGGT | GGAGGAGATT | 780 |
| TGAGGATACA | GATGGCGGCG | GACTCCGCTG | GAGGGTCTTC | ATCTGGGAAG | AGCTGGGCGC | 840 |
| AGCAGACGGA | GGAGAGTTAT | CAGCTGCAGC | TTGCATTGGC | GTTAAGGCTT | TCGTCGGAGG | 900 |
| CTACTTGTGC | CGACGATCCG | AACTTTCTGG | ATCCTGTACC | GGACGAGTCT | GCTTTACGGA | 960 |
| CTTCGCCAAG | TTCAGCCGAA | ACCGTTTCAC | ATCGTTTCTG | GGTATTTGTT | CCTGTTAAGC | 1020 |
| TTTGTTTCCC | AAAATTATTG | AATCGTGGTT | ATAGAGATAT | GGTCCTCTTG | TTTCCGAAGT | 1080 |
| TTCAGTTAGA | TCTCCTTACC | AAAAGTCTAT | TAGTAGCAAA | TGAGATATGT | TGTTTAGATA | 1140 |
| CATTGCAGAG | TATGATTGTT | TTGTGTGCTG | CATCAGGTTA | ATGGCTGCTT | ATCGTACTAT | 1200 |
| GATAAAGTTC | CTGATGGGTT | TTATATGATG | AATGGTCTGG | ATCCTATAT | TTGGACCTTA | 1260 |
| TGCATCGACC | TGCATGAAAG | TGGTCGCATC | CCTTCAATTG | AATCATTAAG | AGCTGTTGAT | 1320 |
| TCTGGTGTTG | ATTCTTCGCT | TGAAGCGATC | ATAGTTGATA | GGCGTAGTGA | TCCAGCCTTC | 1380 |
| AAGGAACTTC | ACAATAGAGT | CCACGACATA | TCTTGTAGCT | GCATTACCAC | AAAAGAGGTT | 1440 |
| GTTGATCAGC | TGGCAAAGCT | TATCTGCAAT | CGTATGGGGT | TTGTACTCAT | ACAATCCTTA | 1500 |
| CTATCCCTTT | GAACTTATAT | TTTTATATCT | TCCTGTGATT | TCTCACATTG | TACTCGTTAA | 1560 |
| TTCTTGCTTC | CCCAGGGGTC | CAGTTATCAT | GGGGGAAGAT | GAGTTGGTTC | CATGTGGAA | 1620 |
| GGAGTGCATT | GATGGTCTAA | AAGAAATCTT | TAAAGTGGTG | GTTCCCATAG | GTAGCCTCTC | 1680 |
| TGTTGGACTC | TGCAGACATC | GAGCTTTACT | CTTCAAAGTG | AGATCCCAAC | TTTGATGCTA | 1740 |
| TCCCCATGAC | ATTTAAGACA | TCTTGTGAAA | TGATCATATA | AATTATTGTG | CTTCATCCAT | 1800 |
| TTGTTTTTAT | TGGAATACAT | ATGAAGAACG | TTGAATGTGA | AAAGTGGTGT | TATTGATTAG | 1860 |
| AAAAAAATAG | GTTACTGATA | GTTGAATGTT | CCAAAGAAAA | AAAGTATTTT | ATATCTTCTA | 1920 |
| TTTGGTGCAT | GCAGGTACTG | GCTGACATAA | TTGATTTACC | CTGTCGAATT | GCCAAAGGAT | 1980 |
| GTAAATATTG | TAATAGAGAC | GATGCCGCTT | CGTGCCTTGT | CAGGTTTGGG | CTTGATAGGT | 2040 |
| ATGATACAAG | TGATTGCGAA | AGAGCCTTTA | TTTTCCTATT | TTCTTTGCTT | TTTGTTTCTG | 2100 |
| GAAAAACAAT | TATAGCTCCA | AATGTTTCGC | AGAATATTAG | GTTGATGACG | TGGAAAATTT | 2160 |
| GTTTTGGTTT | CAGGGAGTAC | CTGGTTGATT | TAGTAGGAAA | GCCAGGTCAC | TTATGGGAGC | 2220 |
| CTGATTCCTT | GCTAAATGGT | CCTTCATCTA | TCTCAATTTC | TTCTCCTCTG | CGGTTTCCAC | 2280 |
| GACCAAAGCC | AGTTGAACCC | GCAGTCGATT | TTAGGTTACT | AGCCAAACAA | TATTTCTCCG | 2340 |
| ATAGCCAGTC | TCTTAATCTT | GTTTTCGATC | CTGCATCAGG | TATTCCCATA | CAAAAAACCT | 2400 |

```
GAATAATATG TTAACTTTTT GCATGCTGCT TACATCTCGT TTTGTATTTC CCCTAAAAGA    2460
GTAATCTCCT ATCATTTAGG GTATTTCTTG ATCATGTCTC AGTATCTGAA GTGTTAGTAG    2520
TCTTAGAATG ATTCTATTGT TTGTTTTCTT GTCTCTTTTC ACTTTAGTTG TTTTTGGCTG    2580
TTGATGTGTA TGTTTGTTGG TGGGTTCTTT GCCTAATGAT ATTTAAGGTT AAACTTGTTA    2640
GTCTGCTGTT CAAGCTTATG AATTCTAGTG CATTTATGTG CAAGACTTGT CTTCTGGACT    2700
CTAATTTCTT ATATCTGCTT GTTTGAATGG TTGTAGATGA TATGGGATTC TCAATGTTTC    2760
ATAGGCAATA TGATAATCCG GGTGGAGAGA ATGACGCATT GGCAGAAAAT GGTGGTGGGT    2820
CTTTGCCACC CAGTGCTAAT ATGCCTCCAC AGAACATGAT GCGTGCGTCA ATCAAATTG     2880
AAGCAGCACC TATGAATGCC CCACCAATCA GTCAGCCAGT TCCAAACAGG GCAAATAGGG    2940
AACTTGGACT TGATGGTGAT GATATGGACA TCCCGTGGTG TGATCTTAAT ATAAAGAAA     3000
AGATTGGAGC AGGTAATAAT TTTACGAAA AATTAATGAT TCGGTCTAAA AATGCAAAGA    3060
AATATGAAAT TCTTGAGGAA GTGGTTTTGC TTTGGACTCT GTTCTCGAAC AAAATAAGGA    3120
AAAAGTGCCA CCCATTTTGA GATTACATTC TTCTCTGTTG CCTTTAATTC TTCCACTCTA    3180
ATTTGAGCGA CTGCTCTTTC AGGTTCCTTT GGCACTGTCC ACCGTGCTGA GTGGCATGGC    3240
TCGGTAAGAA CTTTTTTGTC AGAATTTACG CAGCTGAATT TTTTTTCGCT CTAAAAATTT    3300
GGTTGTGACT TTTGGATCTG CTTGGTATTA TAAAAGGCAA AGTTATTGTA TATGTGACTC    3360
TCCGTTCTGT CAGAAATTAA ACACGGACAA AAGGTGTCCC ATTTTAGATG TATATGTGTC    3420
TTTATATCAT AAATTTGTCT TCCTGTTTGA ATTTACAAT TCTATCACTA GAAGAATTCT    3480
AATTTGATT ATTGCAGTAA TATTCTCTAT CAATTTCAGG ATGTTGCTGT GAAAATTCTC    3540
ATGGAGCAAG ACTTCCATGC TGAGCGTGTT AATGAGTTCT TAAGAGAGGT GCACAAATAA   3600
AATTTCTCT TGATTTGGT AATGAACTTG TTGTATTAAT GTCTCCAATG ATCTTGATTC     3660
GCTGTCAGGT TGCGATAATG AAACGCCTTC GCCACCCTAA CATTGTTCTC TTCATGGGTG   3720
CGGTCACTCA ACCTCCAAAT TTGTCAATAG TGACAGAATA TTTGTCAAGG TACAATTACT   3780
TGGATTTGGA AGGTTGATG TACTGAGTGT AGAATTTTGG CCTATAATGA CTCTAATACC    3840
ATGATTTCTT TCAAACAGAG GTAGTTTATA CAGACTTTTG CATAAAAGTG GAGCAAGGGA   3900
GCAATTAGAT GAGAGACGTC GCCTGAGTAT GGCTTATGAT GTGGTATGTT TAACTCCTTA   3960
TGTTACATGT ATGGGTGATT ACTTCCTGAT CTTGGTGTTT CTTCACATGG AACTTTCTTT   4020
CCAATTCTCT GTCACAGGCT AAGGGAATGA ATTATCTTCA CAATCGCAAT CCTCCAATTG   4080
TGCATAGAGA TCTAAAATCT CCAAACTTAT TGGTTGACAA AAAATATACA GTCAAGGTTT   4140
GAATCTAAAT TAGAAATTGT TGTGTCCAAT GTTTTGATTT TGATATTTTA TTCCTCTTGT   4200
GAGACAAGCT TATATATAAA TTATGATTTT TAATTCTAAA TTGGTTTGGA GACATTACAA   4260
AAAGGCGTTA ATCTGCTGAA ACTTAAAGA TACAGCAGCC TCAAGCTGTC GTCTTAAAAA    4320
CAATCAGAAC ATTATTATTC TAACTCCTCA ATTTGTCTTG AAATTTCAGG TTTGTGAATT   4380
TGGTCTCTCG CGATTGAAGG CCAGCACGTT TCTTTCCTCG AAGTCAGCAG CTGGAACCGT   4440
AAGTTCAGTT TGTTTGAAAC TAAAACACGC TGAACAACGT AACTTTCTTC TAGGTCCTAT   4500
TTCCAATGGA AGCTAAATAA TTACTGACTT TGATATATCA GCCCGAGTGG ATGGCACCAG   4560
AAGTCCTGCG AGATGAGCCG TCTAATGAAA AGTCAGATGT GTACAGCTTC GGGGTCATCT   4620
TGTGGGAGCT TGCTACATTG CAACAACCAT GGGGTAACTT AAATCCGGCT CAGGTACTTC   4680
CCACTCTAAA CATCCCAAAT AATAATGATA TTATTTTGCA TTTGGAAGTC CCTCACTCTA   4740
CATTTCATAA CATGCTATAT ATGATCATCC AACAAAATGT TCCATAGGTT GTAGCTGCGG   4800
TTGGTTTCAA GTGTAAACGG CTGGAGATCC CGCGTAATCT GAATCCTCAG GTTGCAGCCA   4860
```

-continued

```
TAATCGAGGG  TTGTTGGACC  AAGTACGTTA  AGATTTTCTA  TCTCTTTTTT  GAATTCTTCT   4920
TGAATAGACT  TCATGTTTAT  GTATGTGTTT  CATTACCAGT  GAGCCATGGA  AGCGTCCATC   4980
ATTTGCAACT  ATAATGGACT  TGCTAAGACC  ATTGATCAAA  TCAGCGGTTC  CTCCGCCCAA   5040
CCGCTCGGAT  TTGTAAAATA  CCCCCGGTCC  ATTCAAAAGT  TGTTATAATC  ATGATATGCA   5100
CATATACTCT  CAGCATTCTT  TTGCTGCCCA  GGAGGGAGAC  ACTAGTTAAG  ATATAGCTTT   5160
AAAGGTACAT  TCCTCATGAG  CTATCAATCA  TATCCTACAG  AATCCCATGG  TTTTTATACA   5220
TGTATTATTT  TTGCGATCTT  TGTCTGCTGT  TTTGTTCCCT  TTTTAATGTT  GCAGATTGTT   5280
AAAATGTACA  TGACTATTGT  CACAGGGAGG  AAAAAAAAAT  GTAGTAATGG  AAACAATGTG   5340
AGGGATATAA  TCTATCTATC  TAGTCCCAAA  GGGTAAGCAA  TATTGTGTTG  TTATGTCTTT   5400
GTAGCAATGC  ACTGAAAGCT  ATATTTAATT  ACATTGCTGT  ACATTTATAC  CGCTAAATTA   5460
GTTACTAAGC  GAAGGTAAAA  AAGAGCAGCT  GGTAAATGCT  GTCAAGGGT   TTTGCAAACT   5520
CAATATGATT  CATTGGATTT  ACATTGTTC   ACTGTGCGAT  TAGTCTGGAC  TATAAACCAA   5580
CAGAAATGAA  ATAAGACTGT  AACTTTCGGA  GACTCTAATA  CAGATGAATA  TAATCCCAAA   5640
TCGTTAAAAA  CGCATTGGGA  CTGAAAATAT  CTAGATACAT  AGTCAACTAT  TTTTGCCTTC   5700
GCGTCTAAGT  AAGTTCCCAC  ACTTGAAAAC  GACTTTACCT  GTCTTCCGAA  TTAATCGTTT   5760
GATGGATCGG  TAACCAATAG  GATTGCGTAA  ATCAAAATTA  TACAATATTA  AATTCTGAAA   5820
AAGGAAACAC  GAAAAGCGAA  TCAGTGATTT  GTGAGGGCCC  AGTTCCAAAT  TAGAAAGCTG   5880
ACCTGGCAAA                                                              5890
```

CONSTITUTIVE TRIPLE RESPONSE GENE AND MUTATIONS

REFERENCE TO GOVERNMENT GRANTS

This work was supported in part by research grants from the National Science Foundation, grant number DCB-9008323 and National Institutes of Health, grant numbers GM38894 and GM42471. The United States Government may have certain rights in this invention.

BACKGROUND OF THE INVENTION

Ethylene is one of five well-established plant hormones. It mediates a diverse array of plant responses including fruit ripening, leaf abscission and flower senescence.

The pathway for ethylene biosynthesis has been established (FIG. 1). Methionine is converted to ethylene with S-adenylmethionine (SAM) and 1-aminocyclopropane-1-carboxylic acid (ACC) as intermediates. The production of ACC from SAM is catalyzed by the enzyme ACC synthase. Physiological analysis has suggested that this is the key regulatory step in the pathway. This enzyme has been cloned from several sources (Sato and Theologis, 1989; Van Der Straeten et al., 1990; Nakajima et al., 1990). The conversion of ACC to ethylene is catalyzed by ethylene forming enzyme (EFE), which has been recently cloned (Spanu et al., 1991). Aminoethoxy-vinylglycine (AVG) and $\alpha$-aminoisobutyric acid (AIB) have been shown to inhibit ACC synthase and EFE respectively. Ethylene binding is inhibited non-competitively by silver, and competitively by several compounds, the most effective of which is trans-cyclooctane.

Etiolated dicotyledonous seedlings are normally highly elongated and display an apical arch-shaped structure at the terminal part of the shoot axis; the apical hook. The effect of ethylene on dark grown seedlings, the triple response, was first described in peas by Neljubow in 1901. In Arabidopsis, a typical triple response consists of a shortening and radial swelling of the hypocotyl, an inhibition of root elongation and an exaggeration of the curvature of the apical hook (FIG. 2A). Etiolated morphology is dramatically altered by stress conditions which induce ethylene production the ethylene-induced "triple response" may provide the seedling with additional strength required for penetration of compact soils, see Harpham, N. V. J. et al., *Annals of Bot.*, 68:55 (1991). Ethylene may also be important for other stress responses. ACC synthase gene expression and ethylene production is induced by many types of biological and physical stress, such as wounding and pathogen infection, see Boller, T., in *The Plant Hormone Ethylene*, A. K. Mattoo and J. C. Suttle eds., 293–314 (1991), CRC Press, Inc. Boca Raton and Yu, Y. et al., *Plant Phys.*, 63:589–590 (1979).

A collection of mutants affected in this response has been isolated. One class, the ein mutants (ethylene insensitive), are completely insensitive to ethylene. A second class of mutants are affected in only subset of the seeding responses. The hls1 mutant (hookless) completely lacks an apical hook either in the presence or absence of ethylene.

Constitutive hormone response mutants have been useful in elucidating mechanisms that underlie other hormone-mediated responses (e.g. yeast mating factor, Blinder et al., 1989).

Despite the information known about ethylene biosynthesis, how plants perceive and transduce hormone signals is almost completely unknown. While many of the components found in animal signal transduction chains have been found in plants, including kinases, and G proteins, no definitive correlation of these signal transducers with any hormone signal has been established. Elucidation of the complex role of these signal molecules would be greatly aided by the isolation of gene mutations which are affected in different steps in the signal transduction pathway.

The present invention addresses these important needs. A novel *Arabidopsis thaliana* mutant has been identified that constitutively exhibits seedling and adult ethylene responses in the absence of the hormone. The constitutive triple response (ctr) mutants display the "ethylene" phenotypes even in the presence of inhibitors of ethylene biosynthesis or receptor binding. ctr1 has a dramatically altered adult morphology that can be phenocopied in wild-type plants by growth in 1 ppm ethylene. Seedling and adult ctr1 plants show high-level constitutive expression of mRNAs for all known ethylene-transduction of the ethylene signal. Genetic, molecular and biochemical characterization of the CTR1 gene and protein product is set forth in the present invention. Genetic characterization of the interactions among modulatory components of the ethylene action pathway will provide insight into how plant hormones function. Thus, the quality, quantity and longevity of food, such as fruits and vegetables, and other plant products such as flowers, will be improved for market in both developed and undeveloped countries.

SUMMARY OF THE INVENTION

The present invention is directed to nucleic acid sequences for constitutive triple response, ctr, gene and corresponding amino acid sequence. Several ctr mutations, amino acid sequences and the corresponding protein products are included within the scope of the present invention. The nucleic acid sequences set forth in SEQUENCE ID NUMBERS 1, and 3–6 as well as amino acid sequences set forth in SEQUENCE ID NUMBERS 1 and 2 are particular embodiments of the present invention.

BRIEF DESCRIPTION OF THE FIGURES

FIG. 6A and B exhibits a comparison of ctr1 and known kinase sequences including b-raf, c-raf, a-raf, draf-1, dpyk1, kpyk2 and zmpk1.

DETAILED DESCRIPTION OF THE INVENTION

Figure 1:
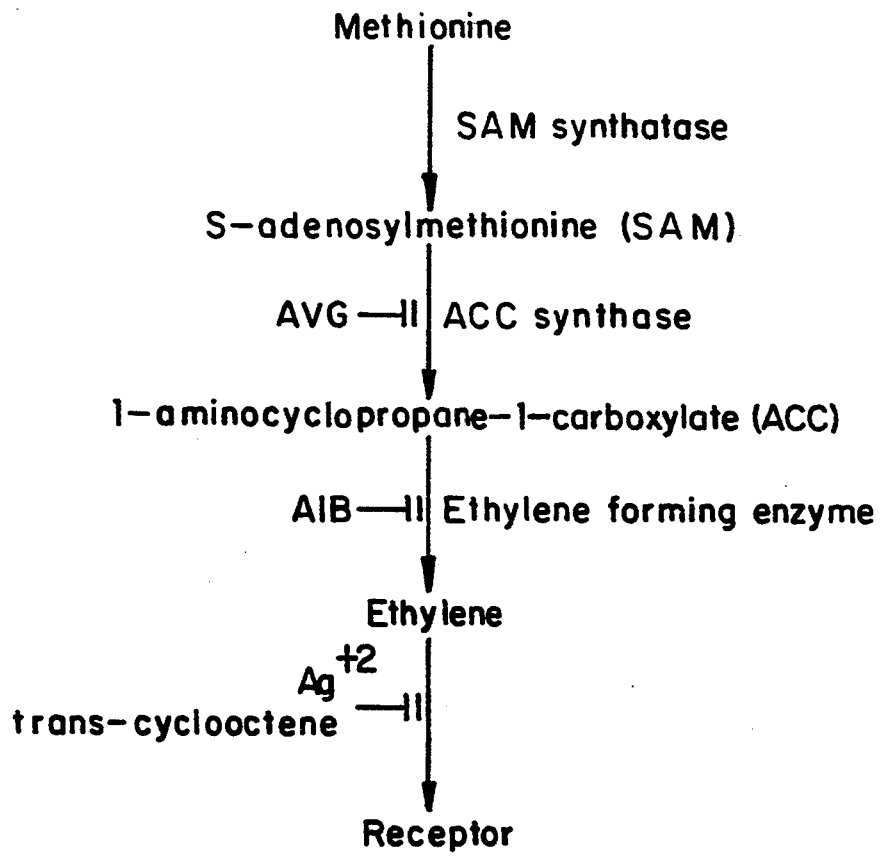
FIG. 1 is a schematic illustration of the ethylene biosynthetic pathway.
Figure 4:
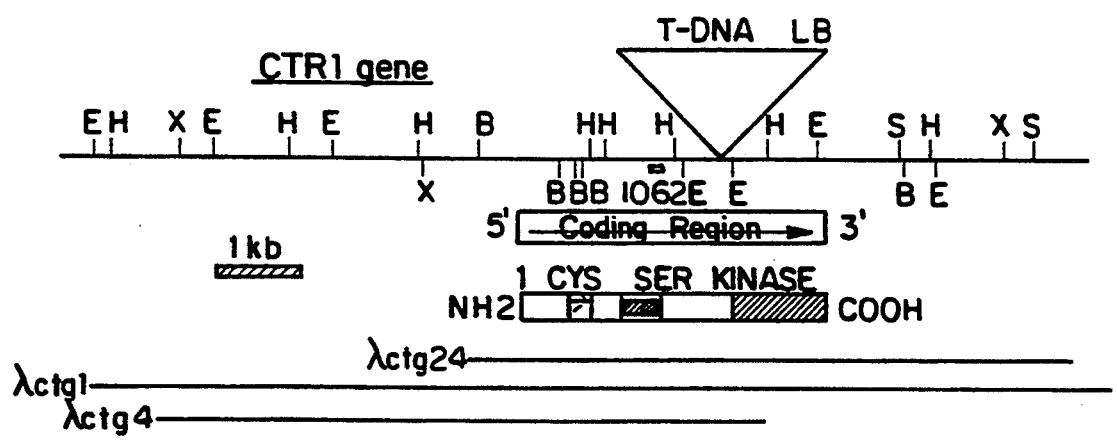
FIG. 4 displays T-DNA insertion into the CTR sequence.

The present invention is directed to constitutive triple response, ctr, nucleic acid sequences and corresponding amino acid sequences. In accordance with the present invention, the CTR gene is identified. Several ctr mutations are included within the scope of the present invention. The nucleic acid sequences set forth in SEQUENCE ID NUMBERS 1, and 3-6 as well as amino acid sequences set forth in SEQUENCE ID NUMBERS 1 and 2 are particular embodiments of the present invention.

Specifically, SEQUENCE ID NO: 1, the isolated cDNA representing the nucleic acid sequence coding for CTR and the isolated genomic CTR DNA sequence of SEQUENCE ID NO: 3 are particularly preferred embodiments of the invention. The purified amino acid sequence of SEQUENCE ID NUMBERS 1 and 2 represent the CTR protein product encoded by the cDNA identified above. The ctr1-2 mutation set forth in SEQUENCE ID NO: 4 has a 17 base pair deletion, from nucleotide positions 2348 to 2364 of CTR genomic DNA sequence in SEQUENCE ID NO: 3. The ctr1-2 mutation of SEQUENCE ID NO: 4 was generated by x-ray mutagenesis. The ctr1-3 mutation set forth in SEQUENCE ID NO: 5 has a "C" to "T" point mutation at nucleotide position 2280 of CTR genomic DNA sequence in SEQUENCE ID NO: 3. The ctr1-3 mutation of SEQUENCE ID NO: 5 was generated by EMS mutagenesis. In the resulting protein product, "arg" is converted to a stop signal. The ctr1-1 mutation set forth in SEQUENCE ID NO: 6 has a "T" to "A" point mutation at nucleotide position 4378 of CTR genomic DNA sequence in SEQUENCE ID NO: 3. The ctr1-1 mutation of SEQUENCE ID NO: 6 was generated by DEB mutagenesis. Another mutation, ctr1-4, was generated by EMS mutagenesis. ctr1-5 comprising the T-DNA insertion in intron 7 after base number 3393 of CTR genomic DNA sequence in SEQUENCE ID NO: 3.

In accordance with the present invention, nucleic acid sequences include and are not limited to DNA, including and not limited to cDNA and genomic DNA; RNA, including and not limited to mRNA and tRNA; and suitable nucleic acid sequences such as those set forth in SEQUENCE ID NOS: 1, and 3-6, and alterations in the nucleic acid sequences including alterations, deletions, mutations and homologs so long as the nucleic acid sequence does not alter the ctr function.

Also amino acid, peptide and protein sequences within the scope of the present invention include, and are not limited to the sequence set forth in SEQUENCE ID NO: 2, the amino acid sequences corresponding to nucleic acids in SEQUENCE ID NOS: 1 and 3-6, and alterations in the amino acid sequences including alterations, deletions, mutations and homologs so long as the amino acid sequence does not alter the ctr function.

In accordance with the invention, the CTR and ctr nucleic acid sequences employed in the invention may be exogenous sequences. Exogenous, as used herein, denotes a nucleic acid sequence which is not obtained from and would not normally form a part of the genetic make-up of the plant or the cell to be transformed, in its untransformed state. Plants comprising exogenous nucleic acid sequences of CTR or ctr mutations, such as and not limited to the nucleic acid sequences of SEQUENCE ID NUMBERS: 1 and 3-6 are within the scope of the invention.

Transformed plant cells comprising nucleic acid sequences of CTR or ctr mutations, such as and not limited to the nucleic acid sequences of SEQUENCE ID NUMBERS: 1 and 3-6, are within the scope of the invention. Transformed cells of the invention may be prepared by employing standard transformation techniques and procedures as set forth in Sambrook et al., *Molecular Cloning: A Laboratory Manual*, 2nd ed., Cold Spring Harbor Laboratory Press, Cold Spring Harbor, N.Y. (1989).

The action of the plant hormone ethylene utilizing the "triple response" of *Arabidopsis thaliana* was studied. The "triple response" in Arabidopsis consists of three distinct morphological changes in dark-grown seedlings upon exposure to ethylene: inhibition of hypocotyl and root elongation, radial swelling of the stem and exaggeration of the apical hook. A class of constitutive mutants, ctr, display a constitutive triple response in the presence of ethylene biosynthetic inhibitors, and is most likely affected at, or downstream of the receptor.

Several ctr alleles have been identified, ctr1-1 to ctr1-5. ctr1 mutants are recessive, do not produce elevated levels of ethylene and have a dramatically altered seedling and adult morphology. The adult phenotype of ctr1 can be phenocopied by growth of wild-type plants in the presence of 1 ppm ethylene and is shown to result, at least in part, to a reduction in cell size.

The present invention is directed to a method of inducing a constitutive triple response in wild-type plants by growing the wild-type plants in the presence of from about 1 ppm to about 10 ppm ethylene for about 2 weeks to about 3 weeks.

At the molecular, cellular and whole plant level, and in seedling and adult plants, air-grown ctr1 mutants strongly resemble ethylene-treated wild-type plants. The recessive nature of ctr suggests that the ethylene-response pathway is normally under negative regulation and loss of function of the CTR repressing activity results in a constitutive triple response phenotype.

The gene corresponding to CTR has been cloned as set forth below and the sequence of cDNA clone is described. The gene encodes a protein that resembles the Raf family of serine/threonine kinases. Physiological, biochemical and genetic evidence indicates that the CTR1 and EIN3 gene products are required for transduction of the ethylene signal in both etiolated seedling and adult plants. The putative CTR1 kinase is postulated to act as a negative regulator in the ethylene signal transduction chain.

Also disclosed herein is a recessive mutation referred to as ein3 which causes insensitivity to ethylene whereas ctr1 results in constitutive activation of all known ethylene responses in the absence of ethylene. EIN3 may act as a positive regulator whereas CTR1 gene product acts as appears to act as a negative regulator in the ethylene action pathway. The predicted protein sequence of EIN3 and EIL1, an EIN3 related gene, are reminiscent of transcription factors. These include acidic and basic domains and mono-amino acid repeat motifs. The EIN3 and EIL1 proteins may be targets for phosphorylation by the CTR1 kinase. Double mutant analysis indicated that the EIN3 gene product acts downstream of the CTR1 gene product in the ethylene signal transduction pathway. CTR1, in turn, acts downstream of EIN2 and EIN1/ETR1.

In accordance with the present invention, the present plants included within the scope of the present invention are higher and lower plants of the Plant Kingdom. Mature plants and seedlings are included in the scope of the invention. A mature plant includes a plant at any stage in development beyond the seedling. A seedling is a very young, immature plant in the early stages of development.

Transgenic plants are included within the scope of the present invention which have a phenotype characterized by the CTR gene or ctr mutations. Particularly preferred plants are those from: the Family Umbelliferae, particularly of the genera Daucus (particularly the species *carota*, carrot) and Apium (particularly the species *graveolens dulce*, celery) and the like; the Family Solanacea, particularly of the genus Lycopersicon, particularly the species *esculentum* (tomato) and the genus Solanum, particularly the species *tuberosum* (potato) and *melongena* (eggplant), and the like, and the genus Capsicum, particularly the species *annum* (pepper) and the like; and the Family Leguminosae, particularly the genus Glycine, particularly the species *max* (soybean) and the like; and the Family Cruciferae, particularly of the genus Brassica, particularly the species *campestris* (turnip), *oleracea* cv Tastie (cabbage), *oleracea* cv Snowball Y (cauliflower) and *oleracea* cv Emperor (broccoli) and the like; the Family Compositae, particularly the genus Lactuca, and the species *sativa* (lettuce), and the genus Arabidopsis, particularly the species *thaliana* (Thale cress) and the like. Of these Families, the most preferred are the leafy vegetables, for example, the Family Cruciferae, especially the genus Arabidopsis, most especially the species *thaliana*.

The present invention will benefit plants in relation to stress. Stress includes, and is not limited to, infection as a result of pathogens such as bacteria, viruses, fungi; wound healing and soil penetration. Bacterial infections include, and are not limited to, *Clavibacter michiganense* (formerly *Coynebacterium michiganense*), *Pseudomonas solanacearum* and *Erwinia stewartii*, and more particularly, *Xanthomonas campestris* (specifically pathovars *campestris* and *vesicatoria*), *Pseudomonas syringae* (specifically pathovars *tomato*, *maculicola*).

In addition to bacterial infections, other examples plant viral and fungal pathogens within the scope of the invention include and are not limited to, tobacco mosaic virus, cauliflower mosaic virus, turnip crinkle virus, turnip yellow mosaic virus; fungi including *Phytophthora infestans*, *Peronospora parasitica*, *Rhizoctonia solani*, *Botrytis cinerea*, *Phoma lingam* (*Leptosphaeria maculans*), and *Albugo candida*.

The present invention is further described in the following examples. These examples are not to be construed as limiting the scope of the appended claims.

EXAMPLE 1

Isolation of Constitutive Mutants

Independent lots of ethyl methanesulfonate (EMS), diepoxybutane (DEB) and X-ray mutagenized seeds were screened for mutants that constitutively display the triple response by plating on agar in the absence of added ethylene in the dark, see Table 1. A total of greater than $10^6$ seedlings were screened in this manner, yielding 400 putative mutants, of which 18 mutants survived and gave seeds. These 18 were retested for this phenotype.

*Arabidopsis thaliana* ecotype Columbia was the parent strain for mutant isolation, with the exception of the T-DNA tagged allele which was isolated from a population developed by Feldman and Marks in the WS ecotype. Marker lines were obtained from the Arabidopsis stock center and were as follows: W11 lu, tt3; W13 ttg, yi; NW85 tt4. Triple response screens were performed on petri plates as described by Guzman and Ecker, "*Exploiting the Triple Response of Arabidopsis to Identify Ethylene-Related Mutants*", *The Plant Cell*, 2:513–523 (1990). EMS mutagenized seeds were obtained as described by Guzman and Ecker, supra. For the DEB mutagenesis, seeds were soaked in water overnight, then soaked in 22 mMDEB for 4 hours, washed extensively and grown in 20 independent lots as above. Plants were generally grown in Metro-mix ® in continuous illumination with fluorescent light at 25° and watered with a 15-16-17 (Nitrogen-phosphorous-potassium) nutrient solution, also known as Peter's lite, every fourth watering.

For growth of adult plants in ethylene, seeds were sown in 6" pots in Metro-mix ® and placed in the growth room in chambers sealed with tape. Hydrocarbon free air or 1 ppm ethylene in air was continuously passed though via rubber tubing at a flow rate of approximately 30 ml/min. for 2-3 weeks.

Figure 2A:
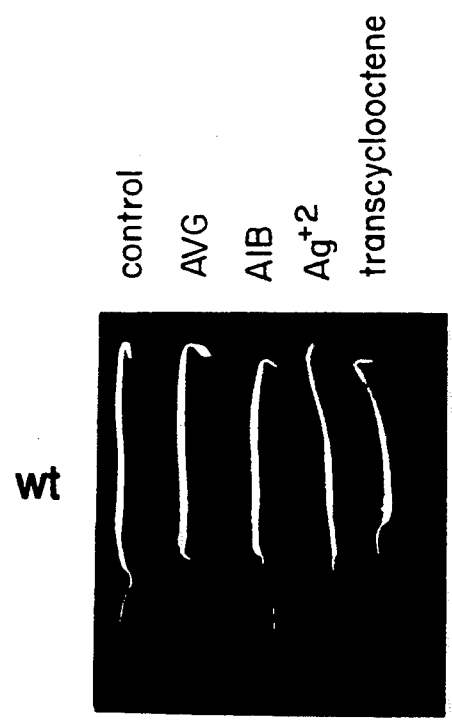
FIG. 2 exhibits the Arabidopsis seedlings, wild-type (FIG. 2A), eto1 (FIG. 2B), and ctr1 (FIG. 2C) controls and seedlings grown in AVG, AIB, $Ag^{+2}$ and transcyclooctene, and control grown in air.
Figure 2B:
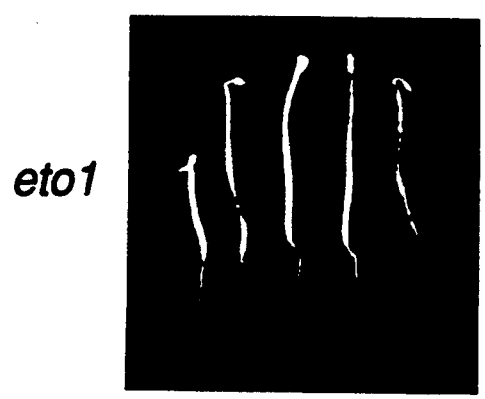
Figure 2C:
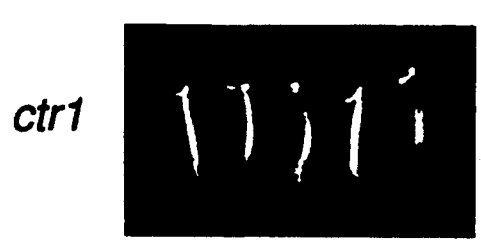
Figure 3:
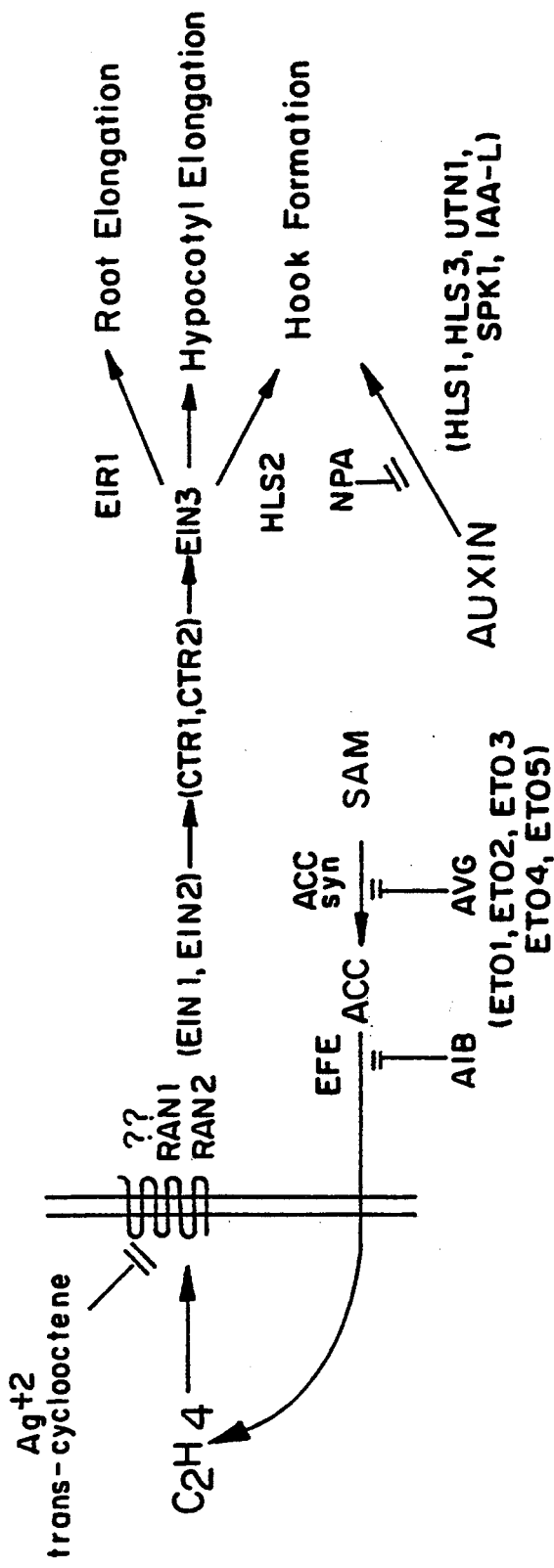
FIG. 3 depicts a pathway model for ethylene signal transduction based on mutational analysis. The proposed sites of dysfunction for the mutations are indicated. The conversion of SAM to ACC is mediated by ACC synthase; a key regulatory step in the biosynthesis of ethylene. Production of ethylene is effectively inhibited by AVG and AIB. The antagonist of ethylene action, trans-cyclooctene, can effectively compete with ethylene for binding sites. $Ag^+$ is a noncompetitive inhibitor of ethylene action. A membrane-localized receptor for ethylene is simply hypothetical.
Figure 5:
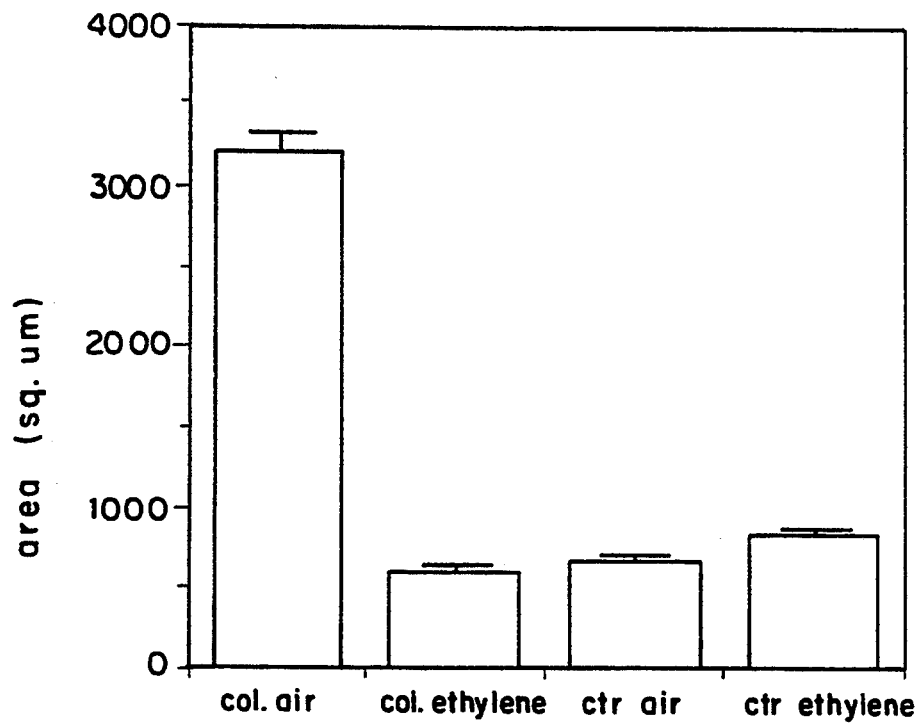
FIG. 5 depicts the area in $\mu m^2$ of epidermal cells. The strains (col. = *Arabidopsis thalia* ecotype Columbia, ctr = constitutes triple response mutants), grown in air or ethylene, correspond to those set forth in Table 3 below.
Figure 8:
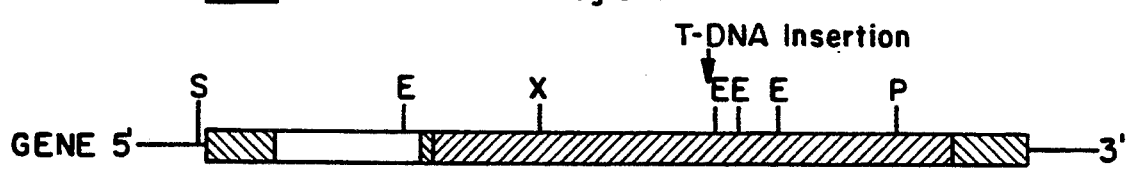
FIG. 8 displays T-DNA insertion into the EIN3 sequence.
Figure 7A:
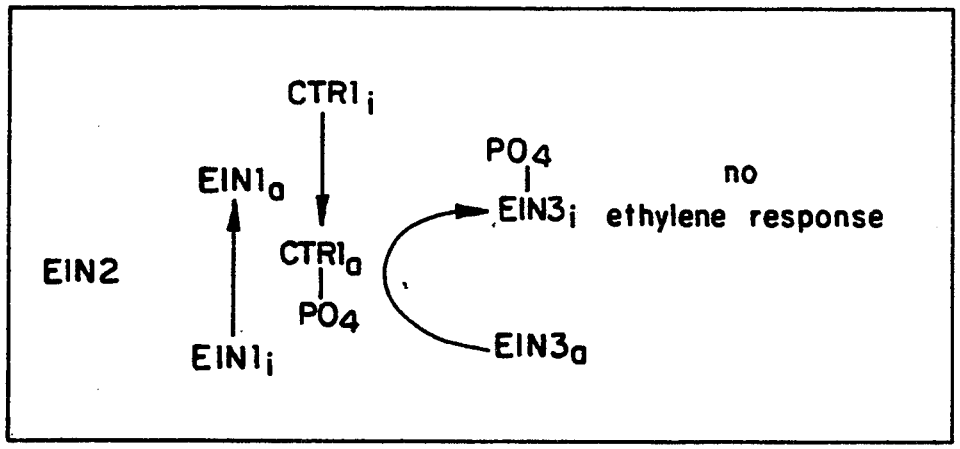
FIG. 7 is a schematic of the effects of the absence (FIG. 7A) and presence (FIG. 7B) of ethylene on ctr1, ein1, ein2 and ein3 mutations in the ethylene response.
Figure 7B:
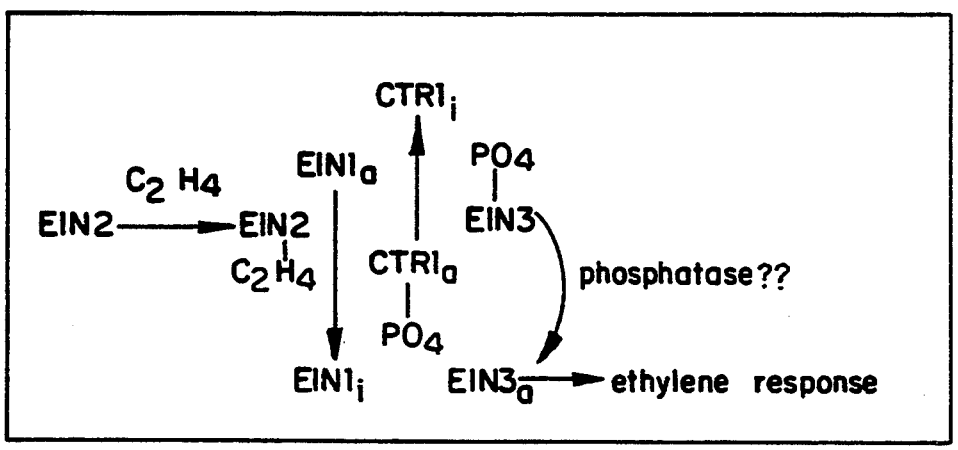

Several inhibitors of ethylene biosynthesis and binding have been described (FIG. 1), and these were examined for their ability to revert the constitutive phenotype of these mutants. Aminoethoxyvinylglycine (AVG), an effective inhibitor of pyridoxal phosphate-mediated enzyme reactions, inhibits ACC synthase, the penultimate step in ethylene biosynthesis which converts S-adenyl-methionine (SAM) to 1-aminocyclopropane-1-carboxylic acid (ACC). α-aminoisobutyric acid (AIB), a structural analog of ACC, has been shown to competitively inhibit the formation of ethylene from ACC. trans-cyclooctene has been shown to be an extremely effective competitive inhibitor of ethylene binding, and silver ion has been shown to be a potent non-competitively inhibitor of ethylene action in several classic ethylene responses. Wild-type and mutant seedlings were grown on agar plates in the presence of these inhibitors at the following concentrations: 10 μM AVG, 0.1 mM AgNO3, 2 mM AIB and trans-cyclooctane (5 μl in 4.4 L in a sealed chamber). The mutants fell into two classes, those in which the constitutive triple response phenotype was efficiently reverted by all four inhibitors and those that were completely unaffected by all four compounds (FIG. 2A, B, and C). This strongly suggested that the constitutive triple response phenotype of the first class was due to an over-production of ethylene, whereas the second class was affected in the perception of ethylene. Measurements of ethylene production confirmed that all the class 1 mutant seedlings, which included the previously identified eto1 mutation, did over-produce ethylene. All of the class 2 mutants fell into a complementation group, ctr1 (see Table 1). The seedling phenotypes of some of these mutants grown in air is shown in FIG. 2A, B and C. A second ctr mutant (ctr2) was also identified that complements ctr1.

EXAMPLE 2
Genetic Analysis of Mutants

Crosses were performed as described Guzman and Ecker, supra. RFLP analysis was performed by crossing ctr1-1 (Columbia background) to a wild-type plant of the Niederzenz ecotype. Individual F3 families were grown and DNA isolated by CsCl banding. The restriction patterns of DNA hybridizing to the RFLP probes from each of the F3 families was analyzed by Southern blotting. DNA probes were prepared by random hexamer labeling.

ctr1 seedlings grown in air are indistinguishable from wild-type seedlings grown in ethylene (FIG. 2A, B, and C). This mutation is recessive and segregates in a manner most consistent with a single Mendelian gene, although it differs significantly from the expected 3:1 ratio as judged by chisquared analysis ($X^2$ Table 1). The mutation maps close to the tt4 and the lu marker on the top of chromosome 5 (Table 2). We also mapped the mutation using restriction fragment length polymorphisms (RFLP). Close linkage was detected with the 447 and the ubq6-1-2 markers (Table 2), on the top of chromosome 5.

TABLE 1
Genetic Analysis of Constitutive Triple Response Mutants

| Cross[a] | Type | Total | Constitutive[b] Triple Res. + | Constitutive[b] Triple Res. − | $X^2$ |
|---|---|---|---|---|---|
| ctr1-1/ctr1-1 X CTR1/CTR1 (DEB)[c] | F1 F2 | 75 1924 | 0 333 | 75 1591 (4.8:1) | 80.8 p < .05 |
| ctr1-2/ctr1-2 X CTR1/CTR1 (X-ray) | F1 F2 | 62 264 | 0 45 | 62 219 (4.9:1) | 8.9 p < .05 |
| ctr1-1/ctr1-1 X ctr1-2/ctr1-2 (X-ray) | F1 | 13 | 13 | 0 | |
| ctr1-1/ctr1-1 X ctr1-3/ctr1-3 (EMS) | F1 | 16 | 16 | 0 | |
| ctr1-1/ctr1-1 X ctr1-4/ctr1-4 (EMS) | F1 | 11 | 11 | 0 | |
| ctr1-1/ctr1-1 X ctr1-5/ctr1-5 (T-DNA) | F1 | 28 | 28 | 0 | |

[a]Crosses were performed as described in Experimental Procedures.
[b]Seedlings were scored for the triple response in the absence of ethylene as described in Experimental Procedures.
[c]Parenthesis indicate mutagen used to generate allele.

EXAMPLE 3
Ethylene-Induced Genes are Constitutively on in the ctr1 Mutant The steady state level of several ethylene-induced transcripts was examined in both seedlings and mature ctr1 plants. EI305 is a random transcript that was isolated by differential screening of ethylene and air treated seedlings. The basic chitinase gene and β1,3 glucanase genes have been shown to be induced by ethylene in adult plants.

Seeds were sterilized and one gram per plate (150 mm) was plated. Seedlings were grown in the dark with either hydrocarbon free air or 10 ppm ethylene blowing through at approximately 30 ml/min for 36 hours. Adult plants were grown in growth chambers until just beginning to bolt, and moved to chambers through which air or 10 ppm ethylene was blowing at approximately 30 ml/min. Total RNA was prepared by extraction with phenol/chloroform, polyA RNA isolated by polyT-cellulose affinity columns and Northern analysis was as described by Sambrook, et al., *Molecular Cloning: A Laboratory Manual*, 2nd ed., Cold Spring Harbor Laboratory Press, Cold Spring Harbor, N.Y. (1989). For size markers, a RNA ladder from Bethesda Research Labs was used.

Results of the northern analysis demonstrated that the steady state level of these ethylene-regulated genes was dramatically increased in air-grown ctr1 seedlings or adult plants. The steady state level of EI305 in air-grown ctr1 seedlings is comparable to wild-type plants grown in 10 ppm ethylene. The basic chitinase gene is also elevated in ctr1 adults, but not to as high a level as ethylene-treated wild-type plants. This may be due to the fact that the wild-type plants are grown in air, then shifted to ethylene, whereas the ctr1 mutants may be acting like plants treated continuously with ethylene.

EXAMPLE 4
Cloning the CTR1 Gens

The CTR was mapped to an interval between two RFLPs on the top of chromosome 5 (Table 2) and a chromosome walk in this area was initiated using a YAC library. In parallel, a T-DNA insertional library was screened for ctr1 matants and a single line was found out of a total of 10,000 screened that segregated for the constitutive triple response phenotype and failed to complement ctr1-1. Genetic analysis showed that the $km^r$ marker on the T-DNA was very closely linked to the ctr1 mutation in this line (Table 2). The T-DNA insertion was very complex; a left border fragment detects greater than ten distinct bands in a Southern blot. The plant DNA flanking the site of insertion was isolated by plasmid rescue of the left border of the T-DNA.

The plant DNA flanking the left border of the T-DNA insertion was isolated by plasmid rescue as follows. DNA was prepared by CsCl purification as described by Sambrook et al., *Molecular Cloning: A Laboratory Manual*, 2nd ed., Cold Spring Harbor Laboratory Press, Cold Spring Harbor, N.Y. (1989) and 5 μg was digested with SalI restriction enzyme. This was extracted once with an equal volume of phenol/CHCl3/isoamyl alcohol (1:1:24), once with CHCl3/isoamyl alcohol and ethanol precipitated. The DNA was resuspended in water and 5 μg was ligated in a 500 μl reaction according to the manufacturer's instructions (Promega). The ligation mix was transformed into HB101 by electroporation and plated on LB plus 100 μg/ml ampicillin (LB Ap). 500 colonies were picked into individual wells of 96 well microtiter plates containing 50 μl LB Ap and grown overnight at 37°. The colonies were then replica plated onto a 150 mm petri plate containing LB Ap and grown overnight. Colony lifts were prepared with HYBRON N+ ® (Amersham), and the filters probed. Nine positive colonies were obtained, a couple of which (ctg1a, ctg1b) showed a restriction pattern that did not match that expected for an inverted repeat of T-DNA. These were then used to probe Southern blots to confirm that they contained plant DNA.

Southern blot analysis of wild-type and ctr1-5 DNA revealed that the insertional line showed an altered size of restriction fragments hybridizing to the probe indicating that the rescued DNA did indeed flank the site of T-DNA insertion. The flanking plant DNA was used to screen genomic and cDNA libraries.

Plant DNA was isolated from ctg1a and used to probe an Arabidopsis genomic library in λEMBL (Clontech) and λDASH (gift of Dr. Nigel Crawford). Restriction maps were made of the clones, two were picked that overlapped and were in opposite orientation and these were used to probe a cDNA library constructed in λZAP II (Stratagens). Clones that hybridized to both probes were picked, and all were found to be similar by restriction pattern. Thirty of these were picked and restriction mapped, ten were sequenced from both ends and two were sequenced completely.

One of the genomic clones detected a RFLP between two different Arabidopsis ecotypes and this was used to map the cloned DNA. This analysis showed that the clones mapped very close to the ubq6-12-1 RFLP (1/154 recombinants), and at, or very close to the ctr1 mutation (0/78 recombinants). Northern blot analysis detected a single transcript of 3.2 bp in seedling and adult plants grown in air and ethylene. The T-DNA line showed two transcripts,-one larger and one smaller than the wild-type transcript, probably due to two different termination signals present in the T-DNA. The size of the CTR1 transcript seen in the Northern blots indicates that several of the cDNA clones are near full length.

To prove that the clones did in fact represent the authentic CTR1 gene, the wild-type and several mutant alleles were sequenced. The cDNA and genomic clones were subcloned into pKS (Stratagene) and exo III deletions were performed as described by Sambrook et al., *Molecular Cloning: A Laboratory Manual*, 2nd ed., Cold Spring Harbor Laboratory Press, Cold Spring Harbor, N.Y. (1989). DNA sequencing was done on a Applied Biosystem automated DNA sequencer (model 370A) using dye terminators as recommended by the manufacturer and also using SEQUENASE ® version 2 as described by the manufacturer (United States Biochemicals). All regions were sequenced on both stands at least one time. Synthetic oligonucleotide primers were made (18-19 bp, at least 50% GC) that would enable the exons to be sequenced. DNA was prepared from the mutant alleles by CsCl purification as described and four sets of primers were used to amplify the CTR1 gene from the mutants using the polymerase chain reaction, PCR. Internal restriction sites in the various PCR products were used to subclone the fragments into pKS and the exons sequenced using the synthetic oligonucleotides. Any alterations in the mutations were re-sequenced from at least two additional independent PCR products. In two cases (ctr1-1, ctr1-4 ), the sequence in question was also sequenced from clones isolated directly from a sublibrary made in λZAPI.

All four of the mutant alleles are associated with sequence alterations in this gens, demonstrating conclusively that the clones correspond to the CTR1 gens. The X-ray allels, ctr1-2, SEQUENCE ID NO: 4, was due to a 17 bp deletion from position 2348 to position 2364 of the genomic sequence of SEQUENCE ID NO: 3. These positions correspond to positions 1488 to 1494 of cDNA of SEQUENCE ID NO: 1. One of the EMS mutants, ctr1-3, SEQUENCE ID NO: 5 was due to a C→T transition, resulting in a stop codon at position 2280 of the genomic sequence. This position corresponds to position 1420 of the eDNA in SEQUENCE ID NO: 1. In the resulting protein product, "arg" is converted to a stop signal. The other two alterations were single codon changes resulting in amino acid substitutions. Specifically, the ctr1-1 mutation set forth in SEQUENCE ID NO: 6 has a "T" to "A" point mutation at nucleotide position 4378 of CTR genomic DNA sequence in SEQUENCE ID NO: 3. The ctr1-1 mutation of SEQUENCE ID NO: 6 was generated by DEB mutagenesis. Another mutation, ctr1-4, was generated by EMS mutagenesis. ctr1-5 comprises the T-DNA insertion was found to be after base position 3393 in intron 7 of the genomic sequence set forth in SEQUENCE ID NO: 3.

The cDNA for the CTR1 gene is shown in SEQ ID NO: 1. Comparison of the cDNA and genomic clones revealed that 13 introns interrupt the CTR1 coding region and that the intron/exon boundaries all fit the consensus for splice donor and acceptor sites fairly well. Approximately 10% (3/31) of the cDNA clones were incompletely spliced as judged by analysis of restriction enzyme digestion patterns. These may represent alternatively spliced products, although only a single transcript is detected by Northern blot analysis.

TABLE 2

| Marker[a] | Mapping of the ctr1 mutation | | | |
|---|---|---|---|---|
| | Progeny Type[b] | Total | Recombinants | Distance[c] |
| Morphological | | | | |
| ttg | F3 (cis) | 228 | 49 | 21.5 ± 6 |
| lu | F2 (trans) | 279 | 2 | 8.0 ± 7 |
| tt4 | F2 (cis) | 250 | 27 | 10.8 ± 3.6 |
| RFLP | | | | |
| 447 | F3[d] | 39 | 0 | 0 ± 4.7 |
| ubq 6-12-1 | F3 | 120 | 1 | 0 ± |
| 217 | | 76 | 2 | 0 ± |
| T-DNA | | | | |
| Km[r] | T3 | 1131 | O km[s] | 0 ± 5 |
| ctr | T4 from a single wt, km[r] T3 plant | 265 | 1 did not segregate ctr[e] | 0.4 m.u. ± 1.7 |

[a]Morphological markers were obtained from the Arabidopsis Stock Center. RFLP markers were kindly provided by E. Meyerwitz.
[b]Progeny were form a cross of a ctr1 mutant to the marker (trans), or a cross of a line mutant for both ctr1 and the marker to wild-type (cis).
[c]Distance is shown with a 95% confidence interval.
[d]The crosses for RFLP analysis were to ecotype Niederzenz.
[e]The single non-segregating line still had T-DNA in the intron as judged by Southern analysis.

EXAMPLE 5

CTR1 is a Member of the RAF Family of Serine/Threonine Kinases

The open reading frame of the longest cDNA clone predicted a protein with a molecular weight of 90,000 Daltons containing no obvious membrane-spanning regions. A search of the Swiss-prot data bank revealed that the carboxyl half of the gene was highly homologous to various protein kinases. Strong homology (>50% aa) to the Raf family of serine/threonine protein kinases was revealed in the carboxy-terminal 300 amino acids; the occurrence of a tyrosine in domain IX of the CTR1 gene is unique to the Raf family members. The 11 subdomains common to all known kinases were highly conserved in the CTR1 gene and homology (49% identity in the kinase domain amino acid numbers 450 to 820) was found to the RAF family of serine/threonine kinases. The occurrence of a tyrosine at amino acid position 735 of CTR protein product resulting from nucleic acid of SEQUENCE ID NO: 2 is unique to RAF family members. The threonine at amino acid position 714 is a strong indicator that the protein is a serine/threonine, rather than a tyrosine kinase, though homology was found to the kyk1 and kyk2 genes from dictyostelium, two putative dual specificity kinases. Weak homology to the RAF genes extends an additional 300 residues upstream of the kinase domain including the presence of a serine rich region in both the RAF genes and CTR1. Also, a cystine finger is present in the 5'half of the RAF gene which is thought to bind to lipids. There is a cystine rich region in CTR1 in the appropriate position, but the spacing of the cystine residues is not consistent with known cystine finger motifs.

The two amino acid substitutions seen in ctr1-1 and ctr1-4 are both in very highly conserved residues in kinases. The ctr1-1 mutation is a highly conservative aspartic acid→glutamic acid change at amino acid position 694, but this residue is invariant in all known kinases. The site of insertion of T-DNA and the 17 base pair deletion in the ctr1-2 x-ray allels are predicted to result in truncation of the CTR1 protein with loss of the kinass domain. The change in ctr1-4 is a valine→glycine change at amino acid position 692, in a residue that is highly conserved in other kinass catalytic domains.

EXAMPLE 6

Ethylene Production from Various Arabidopsis Strains

The amount of ethylene produced by wild-type and a number of matants etiolated seedlings after three days in the dark was tested with a gas chromatograph in accordance with the methods of Guzman and Ecker, 1990, incorporated herein by reference. The constitutive matants that were reversible by inhibitors of ethylene action (the Eto matants) all significantly over-produce ethylene, ranging from 10 fold more than wild-type to over 200 fold. ctr1 mutant seedlings produced less ethylene than wild-type seedlings. The Ein matants have been shown to produce more ethylene than wild-type seedlings. These data suggest that ethylene production is negatively regulated in Arabidopsis seedlings.

EXAMPLE 7

Molecular Analysis of Matants

To determine whether the pEI305 cDNA is expressed and regulated by ethylene in adult plants, Northern blots containing total RNA from ethylene-treated and air-grown wild-type (wt), ctr1 and eto1 plants were hybridized with pEI305. All plants were grown in continuous light and harvested at the onset of bolting. Hormone was applied to a group of plants for 24 hours by placing them in a chamber through which 10 ppm ethylene was passed. pEI305 transcripts are barely detectable in air-grown wild-type plants, and are strongly elevated in hormone-treated plants. Air-treated eto1 adults show an increase level of transcripts relative to air-treated plants, but also show an induction upon ethylene treatment. In air-treated ctr1 adults, pEI305 transcripts are expressed at even higher levels than ethylene-treated wild-type plants, and higher levels still upon ethylene treatment.

EXAMPLE 8

Adult Phenotypes ctr1 adult mutants showed dramatic morphological differences compared to wild-type plants. The mutant plants have rosette leaves that are epinastic and much smaller and darker green, they bolt approximately 1-2 weeks later, the early flowers are infertile, the root system are much less extensive and the inflorescence is much smaller than in wild-type plants. In ctr1 mutant flowers the stigmatal surface matures significantly earlier during development than in wild-type flowers. These adult phenotypes are seen in all 5 independent alleles of ctr1 and in backcrosses co-segregate 100% with ctr1. The T-DNA allels shows the most severe phenotype, though this may be due to the fact this allels was isolated in a different ecotype (WS verses Columbia for the others). The other alleles are very similar, with the exception of ctr1-3, (SEQUENCE ID NO: 5) which is slightly more infertile. The dramatic adult phenotype of ctr1 mutants suggests that this gens product is involved in the ethylene response pathway of both seedlings and adult plants.

EXAMPLE 9

Growth in Ethylene Phenocopies the ctr1 Phenotype

When adult plants are placed in ethylene, mature leaves chloros and then senesce. However, when wild-type and mutant plants were grown to maturity in the continuous presence of ethylene, they exhibited all the morphological characteristics seen in air-grown ctr1 plants, with the exception that ethylene-treated plants had fewer tricomss than their air-grown counterparts. An ethylene-insensitive mutant, ein2 (Guzman and Ecker, supra) failed to display these morphological alterations. This indicates that Arabidopsis can either adapt to the continuous presence of ethylene, or that newly formed leaves show a different response than fully formed leaves. The adult phenotype of the ctr1 mutant most likely represents a constitutive adult ethylene response. Interestingly, when ctr1 mutant, but not wild-type leaves, are excised and placed in the dark for several days they show significant chlorosis, approaching that seen in wild-type leaves excised and placed in ethylene in the dark.

EXAMPLE 10 ctr1 Mutants Show a Reduction in the Size of Leaf Epidermal Cells

Plants were grown in chambers with air or ethylene as described above for three weeks (until just beginning to bolt). Leaves from the third or fourth true set were excised, placed in 95% ethanol and boiled for 5 minutes. The ethanol was removed, replaced with lactophenol (1:1:1:1 of 85% lactic acid, phenol, glycerol and water) and boiled again for 5 minutes. The leaves were then mounted on slides, examined under Nomarski optics and photographed. Cell sizes and shapes were quantitated by tracing photographs (10 leaves per treatment, approximately 30 cells per photograph) using a tracing tablet and the MacMeasure program, a tracing program which quantitated the reduction in cell size.

To determine the basis for the reduction in size seen in ctr1 mutant and ethylene-treated leaves, the sizes of leaf cells were examined by Nomarski microscopy. Epidermal cells from mutant leaves were significantly reduced in size relative to wild-type cells, and this reduction in cell size could be phenocopied by growth of wild-type plants in the continual presence of 1 ppm ethylene. There also was a higher concentration stomata in the mutant and ethylene-grown plants as compared to air-grown wild-type leaves, which is consistent with the hypothesis that stomata are spaced as a function of cell number, not leaf area. The reduction in the size of the epidermal cells was quantitated using a tracing program (MacMeasure), and the area of the ctr1 epidermal cells was fivefold smaller than cells from air-grown wild-type plants, but indistinguishable from wild-type plants grown in ethylene (Table 3). Thus, the smaller size of ctr1 and ethylene-grown wild-type leaves is due at least in part to a reduction in cell size. The ctr1 mutant and ethylene-treated wild-type leaves were also rounder than wild-type leaves from air-grown plants (Table 3). This is consistent with the hypothesis that ethylene is inhibiting cell elongation, and that the ctr1 mutant leaves never fully elongate, as developing unexpanded leaves are smaller and rounder than fully expanded ones.

TABLE 3

| Measurements of Epidermal Cell Size and Shape | | | |
|---|---|---|---|
| Strain | Growth[a] | Cell Area[b] | Shape Factor[c] |
| Wild-type | Air | 3,209 ± 140 | 0.29 ± 0.1 |
|  | Ethylene | 593 ± 24 | 0.69 ± 0.1 |
| ctr1 | Air | 660 ± 23 | 0.63 ± 0.1 |
|  | Ethylene | 830 ± 33 | 0.61 ± 0.1 |

[a] Plants were grown continuously in either blowing air or 1 ppm ethylene
[b] Mean from ten leaves, approximately 25 cells per leaf expressed in $\mu m^2$ ± the standard error of the mean.
[c] The values are from the same sample used for the area measurements, expressed as the mean ± the standard error.

EXAMPLE 11

Complementation Analysis

Complementation and linkage analysis has identified a third distinct recessive ethylene insensitivity locus, designated EIN3. As with ein1 and ein2, ein3 mutants showed insensitivity in all seedling and adult plant ethylene responses. However, unlike ein1 and ein2, genetic analysis revealed that ein3 is epistatic to the constitutive ethylene response mutation. Thus, in the ethylene action pathway of Arabidopsis, the EIN3 gene product acts down-stream of the ETR1/EIN1, EIN2, CTR1 gene products.

Two alleles of the recessive ein3 mutation have been identified. Lack of complementation between ein3 -1, an EMS mutant, and ein3 -2, a T-DNA insertional mutant indicate that they are allelic. The ein3 -2 and ein2 -1 mutations complement one another and thus define separate loci. The F2 generation of an ein1-1 (dominant mutation) X ein3 -2 cross segragates wild-type progeny demonstrating that ein1 and ein3 are not allelic. However, the observed ratio of 10 mutant: 1 wild-type deviates from the expected 13:3 ratio indicative of two independently assorting alleles. These results suggest that ein1 and ein3 are linked or that there is a genetic interaction between the two loci which leads to altered patterns of inheritance.

Various modifications of the invention in addition to those shown and described herein will be apparent to those skilled in the art from the foregoing description. Such modifications are also intended to fall within the scope of the appended claims.

---

What is claimed:

1. An isolated nucleic acid sequence comprising the nucleic acid sequence of SEQUENCE ID NO: 1.

2. The isolated nucleic acid sequence of claim 1 encoding the amino acid sequence of SEQUENCE ID NO: 2.

3. An isolated nucleic acid sequence comprising the nucleic acid sequence of SEQUENCE ID NO: 3.

4. An isolated nucleic acid sequence comprising the nucleic acid sequence of SEQUENCE ID NO: 4.

5. An isolated nucleic acid sequence comprising the nucleic acid sequence of SEQUENCE ID NO: 5.

6. An isolated nucleic acid sequence comprising the nucleic acid sequence of SEQUENCE ID NO: 6.

* * * * *